United States Patent
Tian et al.

(10) Patent No.: US 11,407,841 B2
(45) Date of Patent: Aug. 9, 2022

(54) RECOMBINANT BI-FUNCTIONAL FUSION PROTEIN AND USE THEREOF

(71) Applicant: ImmuneOnco Biopharmaceuticals (Shanghai) Co., Ltd., Shanghai (CN)

(72) Inventors: Wenzhi Tian, Shanghai (CN); Song Li, Shanghai (CN)

(73) Assignee: Immuneonco Biopharmaceuticals (Shanghai) Co., Ltd., Shanghai (CN)

( * ) Notice: Subject to any disclaimer, the term of this patent is extended or adjusted under 35 U.S.C. 154(b) by 288 days.

(21) Appl. No.: 16/489,360

(22) PCT Filed: Mar. 15, 2018

(86) PCT No.: PCT/CN2018/079187
§ 371 (c)(1),
(2) Date: Aug. 28, 2019

(87) PCT Pub. No.: WO2018/166507
PCT Pub. Date: Sep. 20, 2018

(65) Prior Publication Data
US 2020/0095339 A1    Mar. 26, 2020

(30) Foreign Application Priority Data

Mar. 15, 2017 (CN) .......................... 201710151979.6

(51) Int. Cl.
| | | |
|---|---|---|
| *A61K 39/395* | (2006.01) | |
| *C07K 19/00* | (2006.01) | |
| *C07K 14/705* | (2006.01) | |
| *C07K 16/46* | (2006.01) | |
| *C12P 21/02* | (2006.01) | |
| *A61K 38/00* | (2006.01) | |

(52) U.S. Cl.
CPC ...... *C07K 16/468* (2013.01); *C07K 14/70596* (2013.01); *C07K 19/00* (2013.01); *C12P 21/02* (2013.01); *A61K 38/00* (2013.01); *C07K 2317/31* (2013.01); *C07K 2317/56* (2013.01); *C07K 2317/732* (2013.01); *C07K 2317/734* (2013.01)

(58) Field of Classification Search
None
See application file for complete search history.

(56) References Cited

FOREIGN PATENT DOCUMENTS

| WO | 2016022971 | 2/2016 |
|---|---|---|
| WO | 2016024021 | 2/2016 |

OTHER PUBLICATIONS

ISA/CN, International search report and written opinion of PCT/CN2018/079187, the corresponding international application, dated Sep. 20, 2018.
EPO, European search report and written opinion of the counterpart EP Application No. 18768501, dated May 17, 2021.
E.C. Piccione et al., SIRP-Antibody fusion Proteins Selectively Bind and Eiiminate Dual Antigen-Expressing Tumor Cells, Clinicai Cancer Research, vol. 22. No. 20, Apr. 28, 2016, pp. 5109-5119.
Emily C Piccione et al, A bispecific antibody targeting CD47 and CD20 selectively binds and eliminates dual antigen expressing lymphoma cells, MABS vol. 7, No. 5, Jun. 17, 2015, pp. 946-956.
Peter E. Van Bommel et al, CD20-selective inhibition of CD47-SIRPalpha "don't eat me" signaling with a bispecific antibody-derivative enhances the anticancer activity of daratumumab, alemtuzumab and obinutuzumab, Oncoimmunology, vol. 7, No. 2, Oct. 31, 2017, pp. 1-6.
JPO, Office Action of the counterpart JP Application No. 2019-542396, dated Aug. 24, 2021.
CNIPA, First Office Action of the counterpart CN application CN201710151979, dated Mar. 15, 2019.
CNIPA, Second Office Action of the counterpart CN application CN201710151979, dated Jan. 22, 2020.
CNIPA, First Office Action of the counterpart CN application CN201880011334, dated Dec. 3, 2020.
CNIPA, First Office Action of the counterpart CN application CN201880011334, dated May 21, 2021.

*Primary Examiner* — Christine J Saoud
*Assistant Examiner* — Jon M Lockard
(74) *Attorney, Agent, or Firm* — Duane Morris LLP; Thomas L Kowalski; Deborah L. Lu

(57) ABSTRACT

Provided is a bi-functional fusion protein as well as its preparation method and use. The bi-functional fusion protein is composed of a monoclonal anti-human CD20 antibody linked to a first extracellular domain of human SIRPα. It is shown in in vitro tests that the bi-functional fusion protein is capable of binding to human CD20 and CD47 simultaneously, thus killing CD20+ tumor cells via antibody-dependent cell-mediated cytotoxicity and complement-dependent cytotoxicity, and is also capable of blocking CD47-SIRPα interaction such that macrophages are activated to attack tumor cells. The bi-functional fusion protein has evident anti-tumor activities.

8 Claims, 9 Drawing Sheets

Specification includes a Sequence Listing.

```
CAGGTCCAGC TGCAGCAGCC GGGCGCGGAG CTCGTGAAGC CGGGGGCCTC GGTCAAGATG   60
AGCTGCAAGG CCAGCGGCTA CACCTTCACG AGCTACAACA TGCACTGGGT GAAGCAGACC  120
CCGGGCCGGG GGCTGGAGTG GATCGGCGCC ATCTACCCCG GGAACGGCGA CACCAGCTAC  180
AACCAGAAGT TCAAGGGCAA GGCGACCCTG ACGGCGGACA AGTCGAGCAG CACCGCCTAC  240
ATGCAGCTCA GCAGCCTGAC CTCGGAGGAC AGCGCCGTCT ACTACTGCGC CCGGTCCACG  300
TACTACGGCG GCGACTGGTA CTTCAACGTC TGGGGGCCG GCACGACCGT GACCGTGAGC  360
GCGGCTAGCA CCAAGGGCCC ATCGGTCTTC CCCCTGGCAC CCTCCTCCAA GAGCACCTCT  420
GGGGGCACAG CGGCCCTGGG CTGCCTGGTC AAGGACTACT TCCCCGAACC GGTGACGGTG  480
TCGTGGAACT CAGGCGCCCT GACCAGCGGC GTGCACACCT TCCCGGCTGT CCTACAGTCC  540
TCAGGACTCT ACTCCCTCAG CAGCGTGGTG ACCGTGCCCT CCAGCAGCTT GGGCACCCAG  600
ACCTACATCT GCAACGTGAA TCACAAGCCC AGCAACACCA AGGTGGACAA GAGAGTTGAG  660
CCCAAATCTT GTGACAAAAC TCACACATGC CCACCGTGCC CAGCACCTGA ACTCCTGGGG  720
GGACCGTCAG TCTTCCTCTT CCCCCCAAAA CCCAAGGACA CCCTCATGAT CTCCCGGACC  780
CCTGAGGTCA CATGCGTGGT GGTGGACGTG AGCCACGAAG ACCCTGAGGT CAAGTTCAAC  840
TGGTATGTGG ACGGCGTGGA GGTGCATAAT GCCAAGACAA AGCCGCGGGA GGAGCAGTAC  900
AACGCCACGT ACCGTGTGGT CAGCGTCCTC ACCGTCCTGC ACCAAGACTG GCTGAATGGC  960
AAGGAGTACA AGTGCAAGGT CTCCAACAAA GCCCTCCCAG CCCCCATCGC CGCAACCATC 1020
TCCAAAGCCA AAGGGCAGCC CCGAGAACCA CAGGTGTACA CCCTGCCCCC ATCCCGGGAG 1080
GAGATGACCA AGAACCAAGT CAGCCTGACC TGCCTGGTCA AAGGCTTCTA TCCCAGCGAC 1140
ATCGCCGTGG AGTGGGAGAG CAATGGGCAG CCGGAGAACA ACTACAAGAC CACGCCTCCC 1200
GTGCTGGACT CCGACGGCTC CTTCTTCCTC TATTCCAAGC TCACCGTGGA CAAGAGCAGG 1260
TGGCAGCAGG GGAACGTCTT CTCATGCTCC GTGATGCATG AGGCTCTGCA CAACCACTAC 1320
ACGCAGAAGA GCCTCTCCCT GTCTCCGGGC GAGGAGGAGC TGCAGGTGAT TCAGCCTGAC 1380
AAGTCCGTAT CAGTTGCAGC TGGAGAGTCG GCCATTCTGC ACTGCACTGT GACCTCCCTG 1440
ATCCCTGTGG GGCCCATCCA GTGGTTCAGA GGAGCTGGAC CAGCCCGGGA ATTAATCTAC 1500
AATCAAAAAG AAGGCCACTT CCCCCGGGTA ACAACTGTTT CAGAGTCCAC AAAGAGAGAA 1560
AACATGGACT TTTCCATCAG CATCAGTGCC ATCACCCCAG CAGATGCCGG CACCTACTAC 1620
TGTGTGAAGT TCCGGAAAGG GAGCCCTGAC ACGGAGTTTA AGTCTGGAGC AGGCACTGAG 1680
CTGTCTGTGC GTGCCAAACC CTCTGCCCCC GTGGTATCGG GCCCTGCGGC GAGGGCCACA 1740
CCTCAGCACT GA   (SEQ ID NO.1)
```

Fig. 3A

```
CAGATCGTGC TGAGCCAGTC GCCGGCCATC CTCAGCGCGA GCCCCGGCGA GAAGGTCACC   60
ATGACGTGCC GGGCCAGCAG CTCGGTGAGC TACATCCACT GGTTCCAGCA GAAGCCCGGG  120
AGCAGCCCCA AGCCGTGGAT CTACGCCACC AGCAACCTGG CCTCGGGCGT GCCCGTGCGC  180
TTCAGCGGGA GCGGCAGCGG GACCAGCTAC AGCCTGACCA TCTCGCGGGT CGAGGCCGAG  240
GACGCCGCCA CCTACTACTG CCAGCAGTGG ACCTCCAACC CGCCCACGTT CGGCGGCGGC  300
ACCAAGCACG AGCTGAAGCG AACTGTGGCT GCACCATCTG TCTTCATCTT CCCGCCATCT  360
GATGAGCAGT TGAAATCTGG AACTGCCTCT GTTGTGTGCC TGCTGAATAA CTTCTATCCC  420
AGAGAGGCCA AAGTACAGTG GAAGGTGGAT AACGCCCTCC AATCGGGTAA CTCCCAGGAG  480
AGTGTCACAG AGCAGGACAG CAAGGACAGC ACCTACAGCC TCAGCAGCAC CCTGACGCTG  540
AGCAAAGCAG ACTACGAGAA ACACAAAGTC TACGCCTGCG AAGTCACCCA TCAGGGCCTG  600
AGCTCGCCCG TCACAAAGAG CTTCAACAGG GGAGAGTGTT AG   (SEQ ID NO.2)
```

Fig. 3B

```
GAGGAGGAGC TGCAGGTGAT TCAGCCTGAC AAGTCCGTAT CAGTTGCAGC TGGAGAGTCG   60
GCCATTCTGC ACTGCACTGT GACCTCCCTG ATCCCTGTGG GGCCCATCCA GTGGTTCAGA  120
GGAGCTGGAC CAGCCCGGGA ATTAATCTAC AATCAAAAAG AAGGCCACTT CCCCCGGGTA  180
ACAACTGTTT CAGAGTCCAC AAAGAGAGAA ACATGGACT TTTCCATCAG CATCAGTGCC   240
ATCACCCCAG CAGATGCCGG CACCTACTAC TGTGTGAAGT TCCGGAAAGG GAGCCCTGAC  300
ACGGAGTTTA AGTCTGGAGC AGGCACTGAG CTGTCTGTGC GTGCCAAACC CTCTGCCCCC  360
GTGGTATCGG GCCTGCGGC GAGGCCACA CCTCAGCACG GCGGCGGTGG GAGCGGCGGC    420
GGGGGCTCGC AGGTCCAGCT GCAGCAGCCG GGCGCGGAGC TCGTGAAGCC GGGGGCCTCG  480
GTCAAGATCA GCTGCAAGGC CAGCGGCTAC ACCTTCACGA GCTACAACAT GCACTGGGTG  540
AAGCAGACCC CGGGCCGGGG CTGGAGTGG ATCGGCGCCA TCTACCCCGG GAACGGCGAC   600
ACCAGCTACA ACCAGAAGTT CAAGGGCAAG GCGACCCTGA CGGTGGACAA GTCGAGCAGC  660
ACCGCCTACA TGCAGCTCAG CAGCCTGACC TCGGAGGACA GCGCCGTCTA CTACTGCGCC  720
CGGTCCACGT ACTACGGCGG CGACTGGTAC TTCAACGTCT GGGGGGCCGG CACGACCGTG  780
ACCGTGAGCG CGGCTAGCAC CAAGGGCCCA TCGGTCTTCC CCCTGGCACC CTCCTCCAAG  840
AGCACCTCTG GGGGCACAGC GGCCCTGGGC TGCCTGGTCA AGGACTACTT CCCCGAACCG  900
GTGACGGTGT CGTGGAACTC AGGCGCCCTG ACCAGCGGCG TGCACACCTT CCCGGCTGTC  960
CTACAGTCCT CAGGACTCTA CTCCCTCAGC AGCGTGGTGA CCGTGCCCTC CAGCAGCTTG 1020
GGCACCCAGA CCTACATCTG CAACGTGAAT CACAAGCCCA GCAACACCAA GGTGGACAAG 1080
AGAGTTGAGC CCAAATCTTG TGACAAAACT CACACATGCC CACCGTGCCC AGCACCTGAA 1140
CTCCTGGGGG GACCGTCAGT CTTCCTCTTC CCCCCAAAAC CCAAGGACAC CCTCATGATC 1200
TCCCGGACCC CTGAGGTCAC ATGCGTGGTG GTGGACGTGA GCCACGAAGA CCCTGAGGTC 1260
AAGTTCAACT GGTATGTGGA CGGCGTGGAG GTGCATAATG CCAAGACAAA GCCGCGGGAG 1320
GAGCAGTACA ACGCCACGTA CCGTGTGGTC AGCGTCCTCA CCGTCCTGCA CCAAGACTGG 1380
CTGAATGGCA AGGAGTACAA GTGCAAGGTC TCCAACAAAG CCCTCCCAGC CCCCATCGCC 1440
GCAACCATCT CCAAAGCCAA AGGGCAGCCC CGAGAACCAC AGGTGTACAC CCTGCCCCCA 1500
TCCCGGGAGG AGATGACCAA GAACCAAGTC AGCCTGACCT GCCTGGTCAA AGGCTTCTAT 1560
CCCAGCGACA TCGCCGTGGA GTGGGAGAGC AATGGGCAGC CGGAGAACAA CTACAAGACC 1620
ACGCCTCCCG TGCTGGACTC CGACGGCTCC TTCTTCCTCT ATTCCAAGCT CACCGTGGAC 1680
AAGAGCAGGT GGCAGCAGGG GAACGTCTTC TCATGCTCCG TGATGCATGA GGCTCTGCAC 1740
AACCACTACA CGCAGAAGAG CCTCTCCCTG TCTCCGGGCA AATGA (SEQ ID NO.11)
```

Fig. 3C

```
CAGATCGTGC TGAGCCAGTC GCCGGCCATC CTCAGCGCGA GCCCCGGCGA GAAGGTCACC   60
ATGACGTGCC GGGCCAGCAG CTCGGTGAGC TACATCCACT GGTTCCAGCA GAAGCCCGGG  120
AGCAGCCCCA AGCCGTGGAT CTACGCCACC AGCAACCTGG CCTCGGGCGT GCCCGTGCGC  180
TTCAGCGGGA GCGGCAGCGG GACCAGCTAC AGCCTGACCA TCTCGCGGGT CGAGGCCGAG  240
GACGCCGCCA CCTACTACTG CCAGCAGTGG ACCTCCAACC CGCCCACGTT CGGCGGCGGC  300
ACCAAGCACG AGCTGAAGCG AACTGTGGCT GCACCATCTG TCTTCATCTT CCCGCCATCT  360
GATGAGCAGT TGAAATCTGG AACTGCCTCT GTTGTGTGCC TGCTGAATAA CTTCTATCCC  420
AGAGAGGCCA AAGTACAGTG GAAGGTGGAT AACGCCCTCC AATCGGGTAA CTCCCAGGAG  480
AGTGTCACAG AGCAGGACAG CAAGGACAGC ACCTACAGCC TCAGCAGCAC CCTGACGCTG  540
AGCAAAGCAG ACTACGAGAA ACACAAAGTC TACGCCTGCG AAGTCACCCA TCAGGGCCTG  600
AGCTCGCCCG TCACAAAGAG CTTCAACAGG GGAGAGTGTT AG  (SEQ ID NO.12)
```

Fig. 3D

```
QVQLQQPGAELVKPGASVKMSCKASGYTFTSYNMHWVKQTPGRGLEWIGAIYPGNGDTSY    60
NQKFKGKATLTADKSSSTAYMQLSSLTSEDSAVYYCARSTYYGGDWYFNVWGAGTTVTVS   120
AASTKGPSVFPLAPSSKSTSGGTAALGCLVKDYFPEPVTVSWNSGALTSGVHTFPAVLQS   180
SGLYSLSSVVTVPSSSLGTQTYICNVNHKPSNTKVDKRVEPKSCDKTHTCPPCPAPELLG   240
GPSVFLFPPKPKDTLMISRTPEVTCVVVDVSHEDPEVKFNWYVDGVEVHNAKTKPREEQY   300
NATYRVVSVLTVLHQDWLNGKEYKCKVSNKALPAPIAATISKAKGQPREPQVYTLPPSRE   360
EMTKNQVSLTCLVKGFYPSDIAVEWESNGQPENNYKTTPPVLDSDGSFFLYSKLTVDKSR   420
WQQGNVFSCSVMHEALHNHYTQKSLSLSPGEEELQVIQPDKSVSVAAGESAILHCTVTSL   480
IPVGPIQWFRGAGPARELIYNQKEGHFPRVTTVSESTKRENMDFSISISAITPADAGTYY   540
CVKFRKGSPDTEFKSGAGTELSVRAKPSAPVVSGPAARATPQH                    583
(SEQ ID NO.3)
```
Fig. 4A

```
QIVLSQSPAILSASPGEKVTMTCRASSSVSYIHWFQQKPGSSPKPWIYATSNLASGVPVR    60
FSGSGSGTSYSLTISRVEAEDAATYYCQQWTSNPPTFGGGTKHELKRTVAAPSVFIFPPS   120
DEQLKSGTASVVCLLNNFYPREAKVQWKVDNALQSGNSQESVTEQDSKDSTYSLSSTLTL   180
SKADYEKHKVYACEVTHQGLSSPVTKSFNRGEC                              213
(SEQ ID NO.4)
```
Fig. 4B

```
EEELQVIQPDKSVSVAAGESAILHCTVTSLIPVGPIQWFRGAGPARELIYNQKEGHFPRV    60
TTVSESTKRENMDFSISISAITPADAGTYYCVKFRKGSPDTEFKSGAGTELSVRAKPSAP   120
VVSGPAARATPQHGGGGSGGGGSQVQLQQPGAELVKPGASVKMSCKASGYTFTSYNMHWV   180
KQTPGRGLEWIGAIYPGNGDTSYNQKFKGKATLTADKSSSTAYMQLSSLTSEDSAVYYCA   240
RSTYYGGDWYFNVWGAGTTVTVSAASTKGPSVFPLAPSSKSTSGGTAALGCLVKDYFPEP   300
VTVSWNSGALTSGVHTFPAVLQSSGLYSLSSVVTVPSSSLGTQTYICNVNHKPSNTKVDK   360
RVEPKSCDKTHTCPPCPAPELLGGPSVFLFPPKPKDTLMISRTPEVTCVVVDVSHEDPEV   420
KFNWYVDGVEVHNAKTKPREEQYNATYRVVSVLTVLHQDWLNGKEYKCKVSNKALPAPIA   480
ATISKAKGQPREPQVYTLPPSREEMTKNQVSLTCLVKGFYPSDIAVEWESNGQPENNYKT   540
TPPVLDSDGSFFLYSKLTVDKSRWQQGNVFSCSVMHEALHNHYTQKSLSLSPGK         594
(SEQ ID NO.13)
```
Fig. 4C

```
QIVLSQSPAILSASPGEKVTMTCRASSSVSYIHWFQQKPGSSPKPWIYATSNLASGVPVR    60
FSGSGSGTSYSLTISRVEAEDAATYYCQQWTSNPPTFGGGTKHELKRTVAAPSVFIFPPS   120
DEQLKSGTASVVCLLNNFYPREAKVQWKVDNALQSGNSQESVTEQDSKDSTYSLSSTLTL   180
SKADYEKHKVYACEVTHQGLSSPVTKSFNRGEC                              213
(SEQ ID NO.10)
```
Fig. 4D

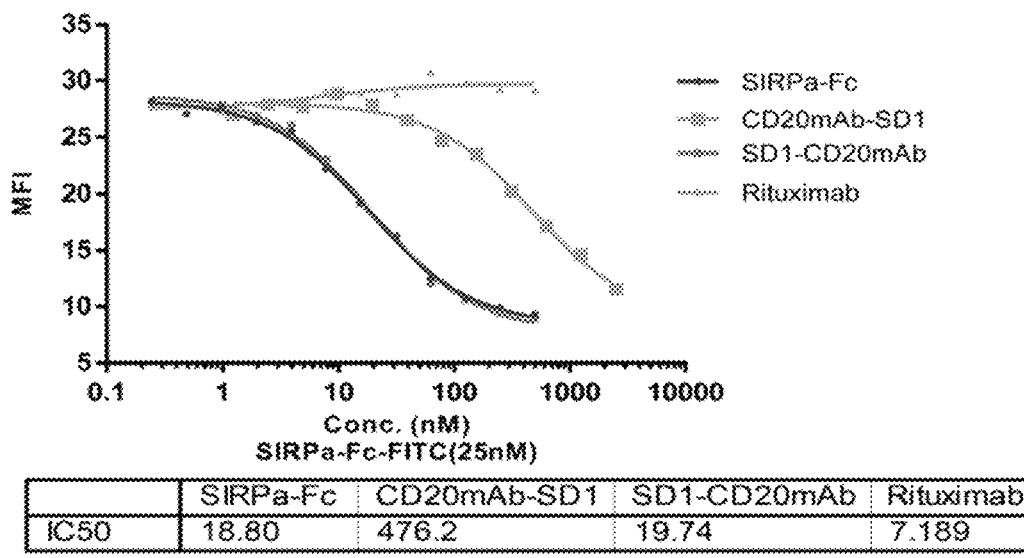
Fig. 7
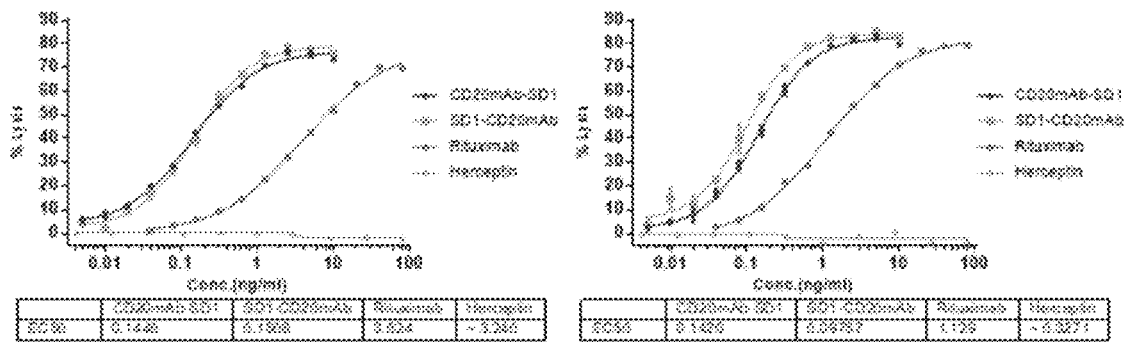
C. CDC Activity
D. CDC Activity
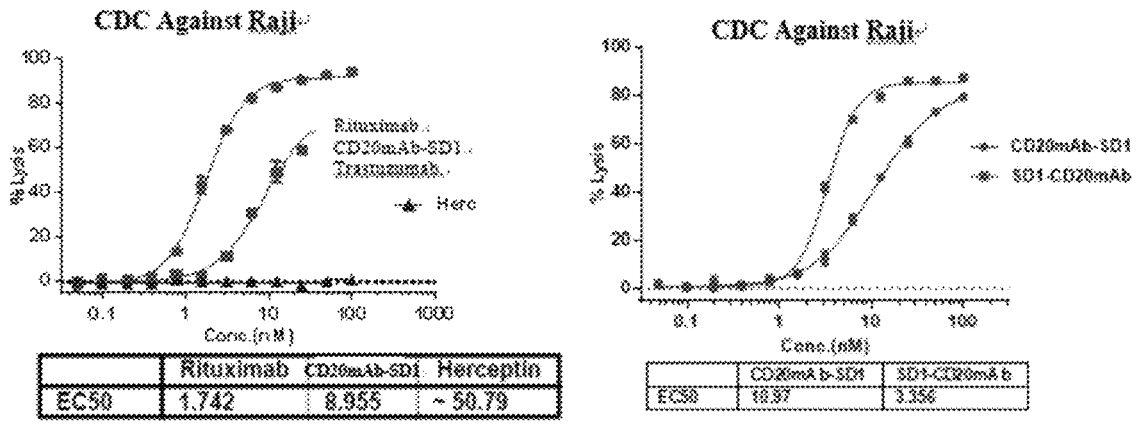
Fig. 8

RECOMBINANT BI-FUNCTIONAL FUSION PROTEIN AND USE THEREOF

FIELD OF THE INVENTION

The present disclosure is related to the biomedical filed, and specifically to a novel recombinant bi-functional fusion protein and the preparation method therefor and the use thereof.

SEQUENCE STATEMENT

The instant application contains a Sequence Listing, which has been submitted electronically and is hereby incorporated by refrence in its entirety. Said ASCII copy is named 55525-00017SequenceListing.txt and is 58,449 bytes in size.

BACKGROUND OF THE INVENTION

CD20 is a transmembrane protein expressed on the cell surfaces of B lymphocytes. Its biological function is not clear till now, and may function as a calcium channel to enable B lymphocyte immune response. CD20 is expressed on the cell membranes of all B cells except the pro-B cells and plasma cells. It is also found on B-cell lymphomas, B-cell chronic lymphocytic leukemia, hairy cell leukemia and melanoma cancer stem cells. Anti-CD20 antibodies that are approved and available on market include Rituximab, Obinutuzumab, and Ofatumumab. These antibodies induce ADCC and CDC. However, it has been found in clinic that CD20s may fall off the cells in certain patients receiving the treatment for a period of time and the patients become no longer sensitive to these antibodies. Some other patients may express Fc-gamma-158F receptors with low affinity (FcγRIIIA-158F) and have certain tolerance to Rituxan®. Therefore, how to address the tolerance issue has become a hot topic in the antibody drug development area.

CD47, also a transmembrane protein, is a member of the immunoglobulin superfamily and expressed on almost all cells including red blood cells. CD47 binds to ligands such as integrin, thrombospondin-1 and signal-regulatory protein (SIRP). CD47 has several biological functions and is involved in cell migration, T cell activation, dendritic cell activation and neuron axon development. Further, CD47 interacts with SIRPα to inhibit macrophage phagocytosis, and thus transmits "don't eat me" signals to prevent phagocytosis of normal cells such as blood cells by macrophages.

Studies have shown that many tumor cells over-express CD47s, which bind to SIRPαs on the surfaces of macrophages to inhibit phagocytosis of tumor cells by macrophages. That is one mechanism the tumors adopt to avoid immune surveillance. Tumors with high CD47 levels include acute myeloid leukemia (AML), chronic myeloid leukemia (CML), acute lymphoblastic leukemia (ALL), non-Hodgkin's lymphoma (NHL), multiple myeloma (MM), bladder cancer, ovarian cancer, prostatic cancer, lung cancer, colon cancer, breast cancer and pancreatic cancer.

Studies showed that the administration of an antibody specific to CD47 that blocks CD47-SIRPα interaction significantly inhibited tumor growth in tumor-bearing mice.

SUMMARY OF THE INVENTION

The present disclosure discloses a novel recombinant bi-functional fusion protein and the preparation method therefor and the use thereof.

In a first aspect, the present disclosure discloses a recombinant bi-functional fusion protein comprising:
a first binding domain (D1); and
a second binding domain (D2);
wherein the first binding domain specifically binds to CD20, and the second binding domain specifically binds to CD47.

In another preferable embodiment, D1 is an antibody or an antibody fragment that specifically binds to CD20.

In another preferable embodiment, D2 is a polypeptide that specifically binds to CD47 and is derived from SIRPα.

In another preferable embodiment, D1 and D2 are connected by a linker peptide. Preferably, the linker peptide contains an antibody constant region.

In another preferable embodiment, D1 and D2 are connected by a linker peptide. Preferably, the linker peptide contains an antibody variable region.

In another preferable embodiment, D1 is a monoclonal anti-CD20 antibody, and D2 is the first extracellular domain of human SIRPα (SIRPα-domain 1, SD1) and linked to the terminus of D1's heavy chain constant region.

In another preferable embodiment, D1 is a monoclonal anti-CD20 antibody, and D2 is the first extracellular domain of human SIRPα (SIRPα-domain 1, SD1) and linked to the terminus of D1's heavy chain variable region.

In another preferable embodiment, the monoclonal anti-CD20 antibody contains a heavy chain variable region of SEQ ID NO.:5 and a light chain variable region of SEQ ID NO.:7.

In another preferable embodiment, the amino acid sequence of D2 is set forth in SEQ ID NO.:9.

In another preferable embodiment, the recombinant bi-functional fusion protein is a homodimer.

In another preferable embodiment, the monoclonal anti-CD20 antibody contains four peptide chains (two heavy chains and two light chains) connected by disulfide bonds, and D2 is linked to the C-terminus or N-terminus of the heavy chain of the monoclonal anti-CD20 antibody.

In a second aspect, the present disclosure discloses a polynucleotide encoding the recombinant bi-functional fusion protein according to the first aspect of the present disclosure.

In a third aspect, the present disclosure discloses a vector containing the polynucleotide according the second aspect of the present disclosure.

In another preferable embodiment, the vector includes a bacterial plasmid, a phage, a yeast plasmid, a plant virus, a mammalian virus such as an adenovirus and a retrovirus, and other vectors.

In a fourth aspect, the present disclosure discloses a genetically engineered host cell containing the vector according to the third aspect or having its genome integrated with the polynucleotide according to the second aspect of the present disclosure.

In a fifth aspect, the present disclosure discloses an immunoconjugate which contains:
(a) the recombinant bi-functional fusion protein according to the first aspect of the present disclosure; and
(b) a second molecule conjugated to the protein of (a), selected from the group consisting of a detectable marker, a drug, a toxin, a cytokine, a radionuclide, and an enzyme.

In another preferable embodiment, the second molecule is selected from the group consisting of a fluorescent or luminous marker, a radioactive marker, a MRI (magnetic resonance imaging) or CT (computed tomography) contrast medium, an enzyme producing a detectable product, a radionuclide, a bio-toxin, a cytokine (such as IL-2), an antibody, an antibody Fc fragment, a single chain antibody fragment (scFv), a gold nanoparticle/nanorod, a virion, a liposome, a magnetic nanoparticle, a prodrug-activating enzyme (such as DT-diaphorase (DTD) or biphenyl hydrolase-like protein (BPHL)), a chemotherapy agent (such as cisplatin), or nanoparticles of any other forms.

In a sixth aspect, the present disclosure discloses a pharmaceutical composition containing:

(i) the recombinant bi-functional fusion protein according to the first aspect of the present disclosure, or the immunoconjugate according to the fifth aspect of the present disclosure; and (ii) a pharmaceutically acceptable carrier.

In another preferable embodiment, the pharmaceutical composition is a parenteral preparation.

In another preferable embodiment, the pharmaceutical composition is used for the preparation of a medicament for treating a tumor. Preferably, the tumor is selected from the group consisting of stomach cancer, liver cancer, leukemia, kidney tumor, lung cancer, small intestinal cancer, bone cancer, prostatic cancer, colorectal cancer, breast cancer, large intestinal cancer, prostatic cancer, cervical cancer, adrenal cancer, and bladder cancer.

In a seventh aspect, the present disclosure discloses the use of the recombinant bi-functional fusion protein according to the first aspect of the present disclosure or the immunoconjugate according to the fifth aspect of the present disclosure in the preparation of a medicament for treating or preventing a CD20-expressing tumor.

In another preferable embodiment, the tumor includes stomach cancer, lymphoma, liver cancer, leukemia, kidney tumor, lung cancer, small intestinal cancer, bone cancer, prostatic cancer, colorectal cancer, breast cancer, large intestinal cancer, prostatic cancer, and adrenal cancer.

In an eighth aspect, the present disclosure discloses a method for preparing the recombinant bi-functional fusion protein, comprising:

(a) culturing the host cells according to the fourth aspect of the present disclosure under a condition suitable for protein expression; and (b) isolating from the cell culture the recombinant bi-functional fusion protein according to the first aspect of the present disclosure.

In a ninth aspect, the present disclosure discloses a method for treating a tumor, comprising administering a subject in need thereof with the recombinant bi-functional fusion protein according to the first aspect of the present disclosure or the immuneconjugate according to the fifth aspect of the present disclosure.

It should be understood that the above-mentioned technical features can be combined with each and every technical feature specifically described hereinafter (for example in the Examples) form new or preferable embodiments, without departing from the scope and spirit of the present disclosure.

DESCRIPTION OF THE DRAWINGS

FIGS. 3A and 3B show the nucleotide sequences of CD20mAb-SD1, with the nucleotide sequence of the heavy chain in FIG. 3A, and the nucleotide sequence of the light chain in FIG. 3B.

FIGS. 3C and 3D show the nucleotide sequences of SD1-CD20mAb, with the nucleotide sequence of the heavy chain in FIG. 3C, and the nucleotide sequence of the light chain in FIG. 3D.

FIGS. 4A and 4B show the amino acid sequences of CD20mAb-SD1, with the amino acid sequence of the heavy chain in FIG. 4A shows, and the amino acid sequence of the light chain in FIG. 4B.

FIGS. 4C and 4D show the amino acid sequences of SD1-CD20mAb, with the amino acid sequence of the heavy chain in FIG. 4C, and the amino acid sequence of the light chain in FIG. 4D.

FIG. 7 shows the recombinant proteins' binding activities to CD47 in an competitive assay.

FIG. 8 shows the ADCC and CDC analysis results, with the recombinant proteins' ADCC activities in Panels A and B, and the recombinant proteins' CDC activities in Panels C and D.

DETAILED DESCRIPTION OF THE INVENTION

Figure 1:
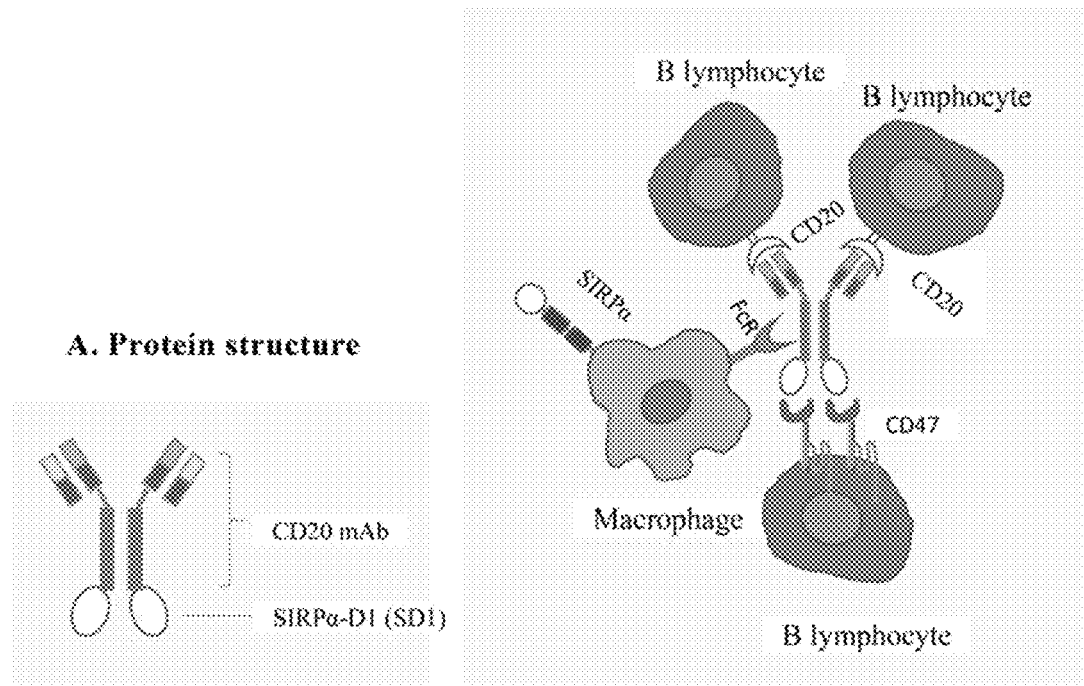
FIG. 1 shows the structure and action mechanisms of CD20mAb-SD1.

With extensive in-depth studies, the inventors of the present disclosure have surprisingly found a recombinant bi-functional fusion protein, namely CD20mAb-SD1, which is composed of a monoclonal anti-human CD20 antibody and a first extracellular domain of human SIRPα(SIRPα-domain 1, SD1). CD20mAb-SD1 is a homodimer with a molecular weight of 180 kDa. After cell line screening, a cell line stably expressing the protein was obtained from Chinese hamster ovary cells (CHO). With fermentation culture of these cells, 500 milligram of such proteins were prepared. In vitro tests showed such proteins may bind to human CD20 and human CD47 simultaneously, thus killing CD20+ tumor cells by inducing antibody-dependent cell cytotoxicity (ADCC) and complement-dependent cytotoxicity (CDC), and promoting macrophages to attack tumor cells by blocking CD47-SIRPα interaction. Also, an in vivo test using human lymphoma model proved CD20Ab-SD1's significant anti-tumor activity. In specific, mice treated by CD20mAb-SD1 achieved 100% survival, while only 67% mice administered with Rituxan® alone survived. Thus, the CD20mAb-SD1 in the present disclosure may be developed as an anti-tumor medicament having excellent efficacy, which can be used to treat patients having B-cell lymphoma or B-cell lymphocytic leukemia that are insensitive or tolerant to Rituxan®.

Prior to the detailed description of the present disclosure, it should be understood that the methods and conditions used in the present disclosure may change and are not limited to those as specifically described. It should be further understood that the terms used herein aim to specify the embodiments and are not to be construed as limiting. The protection scope of the present disclosure is defined by the claims.

Unless otherwise defined, all the technical and science terms used herein have the same meanings known by those skilled in the art. When used with specific numerals, the term "about" means a specific number may have a variation not more than 1%. For example, as used herein, "about 100" refers to all numbers between 99 and 101, such as 99.1, 99.2, 99.3, 99.4 and etc.

Similar or equivalent methods and materials can be used in the embodiments or tests disclosed in the present disclosure, but only preferable methods and materials will be described herein.

SIRPα

Signal-regulatory protein α (SIRPα), also referred to as the substrate of SH2-domain-containing protein tyrosine phosphatase-1, is a transmembrane protein in immunoglobulin superfamily. SIRPα is an important surface receptor for CD47, and CD47-SIRPα signaling plays a negative regulatory role in the immune system.

In one preferable embodiment, the amino acid sequence of the first extracellular domain of SIRPα is set forth below.

(SEQ ID NO. 9)
EEELQVIQPDKSVSVAAGESAILHCTVTSLIPVGPIQWFRGAGPARELIY

NQKEGHFPRVTTVSESTKRENMDFSISISAITPADAGTYYCVKFRKGSPD

TEFKSGAGTELSVRAKPSAPVVSGPAARATPQH

Anti-CD20 Antibody

CD20 is a transmembrane protein expressed on the cell surfaces of B lymphocytes. It is expressed on the cell membranes of all B cells except the pro-B cells and plasma cells, and also found on B-cell lymphomas, B-cell chronic lymphocytic leukemia, hairy cell leukemia and melanoma cancer stem cells. Anti-CD20 antibodies that are approved and available on market include Rituximab, Obinutuzumab, and Ofatumumab. Thus, in a preferable embodiment of the present disclosure, the anti-CD20 antibody for preparing the recombinant bi-functional fusion protein of the present disclosure is selected from the group consisting of Rituximab, Obinutuzumab, and Ofatumumab.

In another preferable embodiment of the present disclosure, the amino acid sequence of the heavy chain variable region of the anti-CD20 antibody is set forth below.

(SEQ ID NO. 5)
QVQLQQPGAELVKPGASVKMSCKASGYTFTSYNMHWVKQTPGRGLEWIGA

IYPGNGDTSYNQKFKGKATLTADKSSSTAYMQLSSLTSEDSAVYYCARST

YYGGDWYFNVWGAGTTVTVSA.

It may be encoded by the nucleotide sequence below.

(SEQ ID NO. 6)
CAGGTCCAGCTGCAGCAGCCGGGCGCGGAGCTCGTGAAGCCGGGGCCTC

GGTCAAGATGAGCTGCAAGGCCAGCGGCTACACCTTCACGAGCTACAACA

TGCACTGGGTGAAGCAGACCCCGGGCCGGGGCTGGAGTGGATCGGCGCC

ATCTACCCCGGGAACGGCGACACCAGCTACAACCAGAAGTTCAAGGGCAA

GGCGACCCTGACGGCGGACAAGTCGAGCAGCACCGCCTACATGCAGCTCA

GCAGCCTGACCTCGGAGGACAGCGCCGTCTACTACTGCGCCCGGTCCACG

TACTACGGCGGCGACTGGTACTTCAACGTCTGGGGGGCCGGCACGACCGT

GACCGTGAGCGCG

In a preferable embodiment of the present disclosure, the amino acid sequence of the light chain variable region of the anti-CD20 antibody is set forth below.

(SEQ ID NO. 7)
QIVLSQSPAILSASPGEKVTMTCRASSSVSYIHWFQQKPGSSPKPWIYAT

SNLASGVPVRFSGSGSGTSYSLTISRVEAEDAATYYCQQWTSNPPTFGGG

TKLEIK

It may be encoded by the nucleotide sequence below.

(SEQ ID NO. 8)
CAGATCGTGCTGAGCCAGTCGCCGGCCATCCTCAGCGCGAGCCCCGGCGA

GAAGGTCACCATGACGTGCCGGGCCAGCAGCTCGGTGAGCTACATCCACT

GGTTCCAGCAGAAGCCCGGGAGCAGCCCCAAGCCGTGGATCTACGCCACC

AGCAACCTGGCCTCGGGCGTGCCCGTGCGCTTCAGCGGGAGCGGCAGCGG

GACCAGCTACAGCCTGACCATCTCGCGGGTCGAGGCCGAGGACGCCGCCA

CCTACTACTGCCAGCAGTGGACCTCCAACCCGCCCACGTTCGGCGGCGGC

ACCAAGCTCGAGATCAAG

In another preferable embodiment of the present disclosure, the amino acid sequence of the heavy chain of the anti-CD20 antibody (CD20mAb-SD1) is as follows.

(SEQ ID NO. 3)
QVQLQQPGAELVKPGASVKMSCKASGYTFTSYNMHWVKQTPGRGLEWIGA

IYPGNGDTSYNQKFKGKATLTADKSSSTAYMQLSSLTSEDSAVYYCARST

YYGGDWYFNVWGAGTTVTVSAASTKGPSVFPLAPSSKSTSGGTAALGCLV

KDYFPEPVTVSWNSGALTSGVHTFPAVLQSSGLYSLSSVVTVPSSSLGTQ

TYICNVNHKPSNTKVDKRVEPKSCDKTHTCPPCPAPELLGGPSVFLFPPK

PKDTLMISRTPEVTCVVVDVSHEDPEVKFNWYVDGVEVHNAKTKPREEQY

NATYRVVSVLTVLHQDWLNGKEYKCKVSNKALPAPIAATISKAKGQPREP

QVYTLPPSREEMTKNQVSLTCLVKGFYPSDIAVEWESNGQPENNYKTTPP

VLDSDGSFFLYSKLTVDKSRWQQGNVFSCSVMHEALHNHYTQKSLSLSPG

EEELQVIQPDKSVSVAAGESAILHCTVTSLIPVGPIQWFRGAGPARELIY

NQKEGHFPRVTTVSESTKRENMDFSISISAITPADAGTYYCVKFRKGSPD

TEFKSGAGTELSVRAKPSAPVVSGPAARATPQH

It may be encoded by the nucleotide sequence below.

(SEQ ID NO. 1)
CAGGTCCAGCTGCAGCAGCCGGGCGCGGAGCTCGTGAAGCCGGGGCCTC

GGTCAAGATGAGCTGCAAGGCCAGCGGCTACACCTTCACGAGCTACAACA

TGCACTGGGTGAAGCAGACCCCGGGCCGGGGCTGGAGTGGATCGGCGCC

ATCTACCCCGGGAACGGCGACACCAGCTACAACCAGAAGTTCAAGGGCAA

GGCGACCCTGACGGCGGACAAGTCGAGCAGCACCGCCTACATGCAGCTCA

-continued

```
GCAGCCTGACCTCGGAGGACAGCGCCGTCTACTACTGCGCCCGGTCCACG
TACTACGGCGGCGACTGGTACTTCAACGTCTGGGGGGCCGGCACGACCGT
GACCGTGAGCGCGGCTAGCACCAAGGGCCCATCGGTCTTCCCCCTGGCAC
CCTCCTCCAAGAGCACCTCTGGGGGCACAGCGGCCCTGGGCTGCCTGGTC
AAGGACTACTTCCCCGAACCGGTGACGGTGTCGTGGAACTCAGGCGCCCT
GACCAGCGGCGTGCACACCTTCCCGGCTGTCCTACAGTCCTCAGGACTCT
ACTCCCTCAGCAGCGTGGTGACCGTGCCCTCCAGCAGCTTGGGCACCCAG
ACCTACATCTGCAACGTGAATCACAAGCCCAGCAACACCAAGGTGGACAA
GAGAGTTGAGCCCAAATCTTGTGACAAAACTCACACATGCCCACCGTGCC
CAGCACCTGAACTCCTGGGGGGACCGTCAGTCTTCCTCTTCCCCCCAAAA
CCCAAGGACACCCTCATGATCTCCCGGACCCCTGAGGTCACATGCGTGGT
GGTGGACGTGAGCCACGAAGACCCTGAGGTCAAGTTCAACTGGTATGTGG
ACGGCGTGGAGGTGCATAATGCCAAGACAAAGCCGCGGGAGGAGCAGTAC
AACGCCACGTACCGTGTGGTCAGCGTCCTCACCGTCCTGCACCAAGACTG
GCTGAATGGCAAGGAGTACAAGTGCAAGGTCTCCAACAAAGCCCTCCCAG
CCCCCATCGCCGCAACCATCTCCAAAGCCAAAGGGCAGCCCCGAGAACCA
CAGGTGTACACCCTGCCCCCATCCCGGGAGGAGATGACCAAGAACCAAGT
CAGCCTGACCTGCCTGGTCAAAGGCTTCTATCCCAGCGACATCGCCGTGG
AGTGGGAGAGCAATGGGCAGCCGGAGAACAACTACAAGACCACGCCTCCC
GTGCTGGACTCCGACGGCTCCTTCTTCCTCTATTCCAAGCTCACCGTGGA
CAAGAGCAGGTGGCAGCAGGGGAACGTCTTCTCATGCTCCGTGATGCATG
AGGCTCTGCACAACCACTACACGCAGAAGAGCCTCTCCCTGTCTCCGGGC
GAGGAGGAGCTGCAGGTGATTCAGCCTGACAAGTCCGTATCAGTTGCAGC
TGGAGAGTCGGCCATTCTGCACTGCACTGTGACCTCCCTGATCCCTGTGG
GGCCCATCCAGTGGTTCAGAGGAGCTGGACCAGCCCGGGAATTAATCTAC
AATCAAAAGAAGGCCACTTCCCCGGGTAACAACTGTTTCAGAGTCCAC
AAAGAGAGAAAACATGGACTTTTCCATCAGCATCAGTGCCATCACCCCAG
CAGATGCCGGCACCTACTACTGTGTGAAGTTCCGGAAAGGGAGCCCTGAC
ACGGAGTTTAAGTCTGGAGCAGGCACTGAGCTGTCTGTGCGTGCCAAACC
CTCTGCCCCCGTGGTATCGGGCCCTGCGGCGAGGGCCACACCTCAGCACT
GA
```

In another preferable embodiment of the present disclosure, the amino acid sequence of the light chain of the anti-CD20 antibody (CD20mAb-SD1) is as follows.

(SEQ ID NO. 4)
QIVLSQSPAILSASPGEKVTMTCRASSSVSYIHWFQQKPGSSPKPWIYAT

SNLASGVPVRFSGSGSGTSYSLTISRVEAEDAATYYCQQWTSNPPTFGGG

TKHELKRTVAAPSVFIFPPSDEQLKSGTASVVCLLNNFYPREAKVQWKVD

NALQSGNSQESVTEQDSKDSTYSLSSTLTLSKADYEKHKVYACEVTHQGL

SSPVTKSFNRGEC

It may be encoded by the nucleotide sequence below.

(SEQ ID NO. 2)
```
CAGATCGTGCTGAGCCAGTCGCCGGCCATCCTCAGCGCGAGCCCCGGCGA
GAAGGTCACCATGACGTGCCGGGCCAGCAGCTCGGTGAGCTACATCCACT
GGTTCCAGCAGAAGCCCGGGAGCAGCCCCAAGCCGTGGATCTACGCCACC
AGCAACCTGGCCTCGGGCGTGCCCGTGCGCTTCAGCGGGAGCGGCAGCGG
GACCAGCTACAGCCTGACCATCTCGCGGGTCGAGGCCGAGGACGCCGCCA
CCTACTACTGCCAGCAGTGGACCTCCAACCCGCCCACGTTCGGCGGCGGC
ACCAAGCACGAGCTGAAGCGAACTGTGGCTGCACCATCGTCTTCATCTT
CCCGCCATCTGATGAGCAGTTGAAATCTGGAACTGCCTCTGTTGTGTGCC
TGCTGAATAACTTCTATCCCAGAGAGGCCAAAGTACAGTGGAAGGTGGAT
AACGCCCTCCAATCGGGTAACTCCCAGGAGAGTGTCACAGAGCAGGACAG
CAAGGACAGCACCTACAGCCTCAGCAGCACCCTGACGCTGAGCAAAGCAG
ACTACGAGAAACACAAAGTCTACGCCTGCGAAGTCACCCATCAGGGCCTG
AGCTCGCCCGTCACAAAGAGCTTCAACAGGGGAGAGTGTTAG
```

In another preferable embodiment of the present disclosure, the amino acid sequence of the heavy chain of the anti-CD20 antibody (SD1-CD20mAb) is as follows.

(SEQ ID NO. 13)
EEELQVIQPDKSVSVAAGESAILHCTVTSLIPVGPIQWFRGAGPARELIY

NQKEGHFPRVTTVSESTKRENMDFSISISAITPADAGTYYCVKFRKGSPD

TEFKSGAGTELSVRAKPSAPVVSGPAARATPQHGGGGSGGGGSQVQLQQP

GAELVKPGASVKMSCKASGYTFTSYNMHWVKQTPGRGLEWIGAIYPGNGD

TSYNQKFKGKATLTADKSSSTAYMQLSSLTSEDSAVYYCARSTYYGGDWY

FNVWGAGTTVTVSAASTKGPSVFPLAPSSKSTSGGTAALGCLVKDYFPEP

VTVSWNSGALTSGVHTFPAVLQSSGLYSLSSVVTVPSSSLGTQTYICNVN

HKPSNTKVDKRVEPKSCDKTHTCPPCPAPELLGGPSVFLFPPKPKDTLMI

SRTPEVTCVVVDVSHEDPEVKFNWYVDGVEVHNAKTKPREEQYNATYRVV

SVLTVLHQDWLNGKEYKCKVSNKALPAPIAATISKAKGQPREPQVYTLPP

SREEMTKNQVSLTCLVKGFYPSDIAVEWESNGQPENNYKTTPPVLDSDGS

FFLYSKLTVDKSRWQQGNVFSCSVMHEALHNHYTQKSLSLSPGK

It may be encoded by the following nucleotide sequence.

(SEQ ID NO. 11)
```
GAGGAGGAGCTGCAGGTGATTCAGCCTGACAAGTCCGTATCAGTTGCAGC
TGGAGAGTCGGCCATTCTGCACTGCACTGTGACCTCCCTGATCCCTGTGG
GGCCCATCCAGTGGTTCAGAGGAGCTGGACCAGCCCGGGAATTAATCTAC
AATCAAAAGAAGGCCACTTCCCCGGGTAACAACTGTTTCAGAGTCCAC
AAAGAGAGAAAACATGGACTTTTCCATCAGCATCAGTGCCATCACCCCAG
CAGATGCCGGCACCTACTACTGTGTGAAGTTCCGGAAAGGGAGCCCTGAC
ACGGAGTTTAAGTCTGGAGCAGGCACTGAGCTGTCTGTGCGTGCCAAACC
CTCTGCCCCCGTGGTATCGGGCCCTGCGGCGAGGGCCACACCTCAGCACG
```

-continued
GCGGCGGTGGGAGCGGCGGCGGGGGCTCGCAGGTCCAGCTGCAGCAGCCG

GGCGCGGAGCTCGTGAAGCGGGGGCCTCGGTCAAGATGAGCTGCAAGGC

CAGCGGCTACACCTTCACGAGCTACAACATGCACTGGGTGAAGCAGACCC

CGGGCCGGGGCTGGAGTGGATCGGCGCCATCTACCCCGGGAACGGCGAC

ACCAGCTACAACCAGAAGTTCAAGGGCAAGGCGACCCTGACGGCGGACAA

GTCGAGCAGCACCGCCTACATGCAGCTCAGCAGCCTGACCTCGGAGGACA

GCGCCGTCTACTACTGCGCCCGGTCCACGTACTACGGCGGCGACTGGTAC

TTCAACGTCTGGGGGCCGGCACGACCGTGACCGTGAGCGCGGCTAGCAC

CAAGGGCCCATCGGTCTTCCCCCTGGCACCCTCCTCCAAGAGCACCTCTG

GGGGCACAGCGGCCCTGGGCTGCCTGGTCAAGGACTACTTCCCCGAACCG

GTGACGGTGTCGTGGAACTCAGGCGCCCTGACCAGCGGCGTGCACACCTT

CCCGGCTGTCCTACAGTCCTCAGGACTCTACTCCCTCAGCAGCGTGGTGA

CCGTGCCCTCCAGCAGCTTGGGCACCCAGACCTACATCTGCAACGTGAAT

CACAAGCCCAGCAACACCAAGGTGGACAAGAGAGTTGAGCCCAAATCTTG

TGACAAAACTCACACATGCCCACCGTGCCCAGCACCTGAACTCCTGGGGG

GACCGTCAGTCTTCCTCTTCCCCCCAAAACCCAAGGACACCCTCATGATC

TCCCGGACCCCTGAGGTCACATGCGTGGTGGTGGACGTGAGCCACGAAGA

CCCTGAGGTCAAGTTCAACTGGTATGTGGACGGCGTGGAGGTGCATAATG

CCAAGACAAAGCCGCGGGAGGAGCAGTACAACGCCACGTACCGTGTGGTC

AGCGTCCTCACCGTCCTGCACCAAGACTGGCTGAATGGCAAGGAGTACAA

GTGCAAGGTCTCCAACAAAGCCCTCCCAGCCCCCATCGCCGAACCATCT

CCAAAGCCAAAGGGCAGCCCCGAGAACCACAGGTGTACACCCTGCCCCCA

TCCCGGGAGGAGATGACCAAGAACCAAGTCAGCCTGACCTGCCTGGTCAA

AGGCTTCTATCCCAGCGACATCGCCGTGGAGTGGGAGAGCAATGGGCAGC

CGGAGAACAACTACAAGACCACGCCTCCCGTGCTGGACTCCGACGGCTCC

TTCTTCCTCTATTCCAAGCTCACCGTGGACAAGAGCAGGTGGCAGCAGGG

GAACGTCTTCTCATGCTCCGTGATGCATGAGGCTCTGCACAACCACTACA

CGCAGAAGAGCCTCTCCCTGTCTCCGGGCAAATGA

In another preferable embodiment, the amino acid sequence of the light chain of the anti-CD20 antibody (SD1-CD20mAb) is as follows.

(SEQ ID NO. 10)
QIVLSQSPAILSASPGEKVTMTCRASSSVSYIHWFQQKPGSSPKPWIYAT

SNLASGVPVRFSGSGSGTSYSLTISRVEAEDAATYYCQQWTSNPPTFGGG

TKHELKRTVAAPSVFIFPPSDEQLKSGTASVVCLLNNFYPREAKVQWKVD

NALQSGNSQESVTEQDSKDSTYSLSSTLTLSKADYEKHKVYACEVTHQGL

SSPVTKSFNRGEC

It may be encoded by the following nucleotide sequence.

(SEQ ID NO. 12)
CAGATCGTGCTGAGCCAGTCGCCGGCCATCCTCAGCGCGAGCCCCGGCGA

GAAGGTCACCATGACGTGCCGGGCCAGCAGCTCGGTGAGCTACATCCACT

GGTTCCAGCAGAAGCCCGGGAGCAGCCCCAAGCCGTGGATCTACGCCACC

AGCAACCTGGCCTCGGGCGTGCCCGTGCGCTTCAGCGGGAGCGGCAGCGG

GACCAGCTACAGCCTGACCATCTCGCGGGTCGAGGCCGAGGACGCCGCCA

CCTACTACTGCCAGCAGTGGACCTCCAACCCGCCCACGTTCGGCGGCGGC

ACCAAGCACGAGCTGAAGCGAACTGTGGCTGCACCATCTGTCTTCATCTT

CCCGCCATCTGATGAGCAGTTGAAATCTGGAACTGCCTCTGTTGTGTGCC

TGCTGAATAACTTCTATCCCAGAGAGGCCAAAGTACAGTGGAAGGTGGAT

AACGCCCTCCAATCGGGTAACTCCCAGGAGAGTGTCACAGAGCAGGACAG

CAAGGACAGCACCTACAGCCTCAGCAGCACCCTGACGCTGAGCAAAGCAG

ACTACGAGAAACACAAAGTCTACGCCTGCGAAGTCACCCATCAGGGCCTG

AGCTCGCCCGTCACAAAGAGCTTCAACAGGGGAGAGTGTTAG

In a preferable embodiment of the present disclosure, the anti-CD20 antibody is a single chain antibody, wherein a heavy chain variable region is linked to a light chain variable region, optionally with a linker peptide therebetween. The linker peptide preferably has 1-15 amino acid residues, and more preferably 3-10 amino acid residues.

Bi-Functional Fusion Proteins CD20mAb-SD1 and SD1-CD20mAb

The inventors of the present disclosure have surprisingly found that the bi-functional fusion protein constructed in the present disclosure (containing a domain specifically binding to CD20 and a domain specifically binding to CD47) has an evident inhibitory effect on CD20+ tumors, and may enhance Rituxan®'s efficacy against CD20+ tumors. The bi-functional fusion protein can be used as a sensitizer to treat CD20+ tumors tolerant to Rituxan®.

Thus, the present disclosure provides a recombinant bi-functional fusion protein containing a first binding domain (also referred to as D1) and a second binding domain (also referred to as D2), wherein D1 specifically binds to CD20, and D2 specifically binds to CD47.

According to the present disclosure, the recombinant bi-functional fusion protein may be a single polypeptide with multiple functions, or a complex containing two or more polypeptides covalently or non-covalently bonded. Obviously, every construct capable of binding to CD20 and CD47 simultaneously may be regarded as a recombinant bi-functional fusion protein.

The recombinant bi-functional fusion protein or its variants may be constructed by conventional molecular biological techniques (for example, genetic engineering and protein expression), as known by the skilled in the art.

In a preferable embodiment of the present disclosure, the domain specifically binding to CD20 is an anti-CD20 antibody containing a heavy chain variable region of SEQ ID NO.: 5 and a light chain variable region of SEQ ID NO.:7.

In a preferable embodiment of the present disclosure, the domain specifically binding to CD47 is derived from SIRPα described above, and preferably the first extracellular domain of SIRPα.

In another preferable embodiment of the present disclosure, in the recombinant bi-functional fusion protein, D2 is linked to the C-terminus or N-terminus of D1. For example, the N-terminus of D2 may be linked to C-terminus or N-terminus of D1. Alternatively, the C-terminus of D2 may be linked to C-terminus or N-terminus of D1. The resulting proteins linked in the above-mentioned manners can be used in combination.

In a preferable embodiment of the present disclosure, the monoclonal anti-CD20 antibody (CD20mAb-SD1) contains four peptide chains (i.e., two heavy chains and two light chains) connected by disulfide bonds, and D2 is linked to the C-terminus of the monoclonal anti-CD20 antibody's heavy chain. Preferably, the polypeptide composed of the heavy chain and D2 has an amino acid sequence of SEQ ID NO.:3, which may be encoded by the polynucleotide sequence of SEQ ID NO.:1, and the light chain has an amino acid sequence of SEQ ID NO.:4, which may be encoded by the polynucleotide sequence of SEQ ID NO.:2.

In a preferable embodiment of the present disclosure, the monoclonal anti-CD20 antibody (SD1-CD20mAb) contains four peptide chains (i.e., two heavy chains and two light chains) connected by disulfide bonds, and D2 is linked to the N-terminus of the monoclonal anti-CD20 antibody's heavy chain. Preferably, the polypeptide composed of the heavy chain and D2 has an amino acid sequence of SEQ ID NO.:13, which may be encoded by the polynucleotide sequence of SEQ ID NO.:11, and the light chain has an amino acid sequence of SEQ ID NO.:10, which may be encoded by the polynucleotide sequence of SEQ ID NO.:12.

Binding Domain

The recombinant fusion protein of the present disclosure contains at least two independent binding domains, D1 and D2. As used herein, the term "binding domain" refers to a peptide, a polypeptide, a nucleic acid molecule, a scaffolding molecule, a peptide-exhibiting molecule, or a peptide-containing construct that can specifically bind to a target protein.

As used herein, the term "specifically binding" means an antigen-binding domain forms a complex with a target antigen with a dissociation constant ($K_D$) of 500 pM or less, and such antigen-binding domain does not substantially bind to other irrelevant proteins under common test conditions. Preferably, an "irrelevant protein" refer a protein, a peptide or a polypeptide having an amino acid identity lower that 95%.

The exemplary antigen-binding domain in the present disclosure may be an antibody, an antigen-binding portion of an antibody, a peptide specifically interacting with a target antigen (e.g., a peptibody), a receptor specifically interacting with a target antigen, a protein containing a ligand-binding portion of a receptor specifically binding to a target antigen, an antigen-binding scaffold (e.g., a DARPin, a HEAT repeat, an armadillo repeat, a tetratricopeptide repeat, and other scaffolding molecules containing naturally occurring repeat proteins, see, e.g., Boersma and Pluckthun, (2011) Curr. Opin. Biotechnol. 22:849-857, and references cited therein), or an aptamer or a portion thereof.

The method for determining the specific binding of one molecule to another is well known in the art, including equilibrium dialysis and surface plasmon resonance. For example, as mentioned herein, the antigen-binding domain refers to a polypeptide binding to a specific antigen or its portion with a $K_D$ less than about 500 pM, about 400 pM, about 300 pM, about 200 pM, about 100 pM, about 90 pM, about 80 pM, about 70 pM, about 60 pM, about 50 pM, about 40 pM, about 30 pM, about 20 pM, about 10 pM, about 5 pM, about 4 pM, about 2 pM, about 1 pM, about 0.5 pM, about 0.2 pM, about 0.1 pM, or about 0.05 pM, as measured by surface plasmon resonance.

As used herein, the term "surface plasmon resonance" refers a technology where the protein concentration change inside a bio-sensor is measured by, for example, a BIA-core™ system (Biacore Life Science, GEHealthcare, Piscataway, N.J.) to analyze the optical phenomenon in a real-time manner.

As used herein, the term "$K_D$" is intended to refer to the dissociation constant regarding specific protein-protein interaction (e.g., antibody-antigen interaction). Unless otherwise specified, the $K_D$ of the present disclosure refers to a $K_D$ measured by surface plasmon resonance at 25° C.

Antibody and Antigen-Binding Fragment

The term "antigen-binding domain" (D1 and/or D2) may contain or consist of an antibody or the antigen-binding fragment thereof. As used herein, the term "antibody" is intended to refer to an antigen-binding molecule or complex which contains at least one complementarity determining region (CDR) specifically binding to or interacting with a specified antigen (e.g., CD20 or CD47). The term "antibody" includes an immunoglobulin containing four peptide chains (two heavy chains (H) and two light chains (L) connected by disulfide bonds) or a polymeric antibody thereof (such as IgM). Each heavy chain contains a heavy chain variable region (abbreviated to HCVR or $V_H$) and a heavy chain constant region. The heavy chain constant region contains three domains, $C_H1$, $C_H2$ and $C_H3$. Each light chain contains a light chain variable region (abbreviated to LCVR or $V_L$) and a light chain constant region. The light chain constant region contains one domain $C_L1$. The $V_H$ region and the $V_L$ region may be further divided to several hypervariable regions, namely complementarity determining regions (CDR), interspersed with regions that are more conserved, termed framework regions (FR). Each $V_H$ or $V_L$ is composed of three CDRs and four FRs, arranged from amino-terminus to carboxy-terminus in the following order: FR1, CDR1, FR2, CDR2, FR3, CDR3, FR4. In different embodiments of the present disclosure, the FRs in the antibody or its antigen binding portion may be the same with those in human germline immunoglobulins, with or without natural or artificial modifications. Conserved amino acid sequences may be identified by aligning two or more CDRs.

D1 and/or D2 in the recombinant bi-functional protein of the present disclosure may contain or consist of an antigen-binding fragment from a complete antibody molecule. As used herein, the "antigen binding portion" or "antigen binding fragment" of an antibody refers to a naturally occurring, obtainable with enzymatic catalysis, synthesized or genetically engineered polypeptide or glycoprotein that specifically binds to an antigen to form a complex. A suitable technique such as the enzymatic digestion or the genetic engineering involving the manipulation of expressions of DNAs encoding antibody variable regions and optionally constant regions, can be used to, for example, obtain an antigen binding fragment from a full-length antibody. Such DNAs are well known, commercially available, obtainable from DNA libraries (including, e.g., the phage display antibody library), and/or readily synthesized. The DNAs may be sequenced and chemically or genetically manipulated to, for example, properly arrange one or more variable regions and/or constant regions, insert codons, produce cysteine residues, or modify, add or delete amino acid residues. Examples of the antigen binding fragment include (i) a Fab fragment; (ii) a F(ab')$_2$ fragment; (iii) a Fd fragment; (iv) a Fv fragment; (v) a single chain Fv (scFc); (vi) a dAb fragment; and (vii) a minimal identifying unit composed of amino acid residues in an antibody supervariable region (e.g., a peptide of an independent complementarity determining region (CDR) such as CDR3), or a FR3-CDR3-FR4 peptide. The term "antigen binding fragment", as used herein, is also intended to encompass other engineered molecules, such as an antibody specific to a domain, a single-domain antibody, an antibody with a missing domain, a chimeric antibody, a CDR grafting antibody, a diabody, a triabody, a tetrabody, a mini antibody, a nanobody (such as an univalent nanobody, a divalent nanobody, and the like), a small modular immune pharmaceutical (SMIP) and a variable region of a shark IgNAR antibody.

The antigen binding fragment of an antibody generally contains at least one variable region. The variable region may be composed of a certain number of amino acid residues, and will usually contain at least one CDR with one or more adjacent frameworks in a reading frame. In an antigen biding fragment containing a $V_H$ domain linked to a $V_L$ domain, the $V_H$ and $V_L$ domains may be arranged in an appropriate order. For example, the variable region may be a dimer and may contain a $V_H$-$V_H$, $V_H$-$V_L$, or $V_L$-$V_L$ structure. Optionally, the antigen binding fragment of an antibody may contain a single $V_H$ or $V_L$ domain.

In some embodiments, the antigen binding fragment of an antibody may contain at least one variable region covalently linked to at least one variable region. Exemplary arrangement of the variable region(s) and the constant region(s) in an antigen binding fragment of an antibody may be: (i) $V_H$-$C_H1$; (ii) $V_H$-$C_H2$; (iii) $V_H$-$C_H3$; (iv) $V_H$-$C_H1$-$C_H2$; (v) $V_H$-$C_H1$-$C_H2$-$C_H3$; (vi) $V_H$-$C_H2$-$C_H3$; (vii) $V_H$-$C_L$; (viii) $V_L$-$C_H1$; (ix) $V_L$-$C_H2$; (x) $V_L$-$C_H3$; (xi) $V_L$-$C_H1$-$C_H2$; (xii) $V_L$-$C_H1$-$C_H2$-$C_H3$; (xiii) $V_L$-$C_H2$-$C_H3$; and (xiv) $V_L$-$C_L$. In any one of the above arrangements, including the exemplary ones, the variable region and the constant region may be linked directly or linked via a complete or part of a hinge region or an adapter region. The hinge region may be composed of at least 2 (for example 5, 10, 15, 20, 40, 60 or more) amino acid residues that link the neighboring variable region and/or constant regions with flexibility or semi-flexibility in a single polypeptide. Further, the antigen binding fragment may include homodimers or heterodimers (or other polymeric antibodies) composed of the variable region-constant region structures mentioned above alone or with additional one or more single $V_H$ or $V_L$ domains via non-covalent bonds such as disulfide bonds.

The recombinant bi-functional fusion protein of the present disclosure may contain or consist of a human antibody and/or a recombinant human antibody or the fragment thereof. As used herein, the term "human antibody" refers to an antibody containing the variable region(s) and the constant region(s) derived from a human germline immunoglobulin. However, the human antibody may contain amino acid residues not encoded by human germline immunoglobulin sequences (for example, within a CDR especially a CDR3) (for example, mutations introduced by random or site-specific mutagenesis in vitro or by somatic mutation in vivo). However, as used herein, the term "human antibody" is not intended to include antibodies in which CDR sequences derived from the germline of another mammalian species (e.g., mouse) have been grafted onto human framework sequences.

The recombinant bi-functional fusion protein may contain or consist of a recombinant human antibody or the antigen binding fragment thereof. As used herein, the term "recombinant human antibody" is intended to include all human antibodies prepared, expressed, produced or isolated by genetic engineering, such as antibodies expressed by recombinant expression vectors transferred to host cells (described in detail hereinafter), antibodies isolated from a recombinant human antibody library (described in detail hereinafter), antibodies isolated from transgenic animals with human immunoglobulin genes (e.g., mice) (see, e.g., Taylor et al., (1992) Nucl. Acids Res. 20:6287-6295), or antibodies prepared, expressed or isolated through other means where human immunoglobulin genes are incorporated into other DNA sequences. Such recombinant human antibodies contain the variable region(s) and constant region(s) derived from human germline immunoglobulin sequences. However, in some embodiments, such recombinant human antibodies may be subject to in vitro mutagenesis (or somatic mutation in vivo in transgenic animals with human immunoglobulin genes). Thus, the amino acid sequences in the $V_H$ and $V_L$ regions of the recombinant antibodies are derived from and related to human germline $V_H$ and $V_L$ sequences but may be not naturally occurring ones.

Tumor Targeting

In another aspect of the present disclosure, the recombinant bi-functional fusion protein may target tumor cells.

The recombinant bi-functional fusion protein may be conjugated to (coupled with) drugs, toxins, radioactive isotopes or some other substances harmful to cell survival. Optionally, the drugs or toxins may not kill cells directly, but make cells susceptible to some other substances. In other embodiments involving tumor targeting, the recombinant bi-functional fusion protein of the present disclosure itself may be not conjugated to drugs, toxins, or radioactive isotopes, but are used in combination with other antigen binding molecules (referred to as helper molecules), such as other anti-tumor antibodies.

In some embodiments of the present disclosure involving tumor targeting, the recombinant bi-functional fusion protein (or the helper antibody) may be conjugated to one or more cytotoxic drugs selected from the group consisting of Calicheamicin, Esperamicin, Methotrexate, Adriamycin, Melphala, Chlorambucil, ARA-C, Vindesine, Mitomycin, Cisplatin, Etoposide, Bleomycin, 5-Fluorouracil, Estramustine, Vincristine, Etoposide, Adriamycin, taxol, Larotaxel, Tesetaxel, Orataxel, Docetaxel, Dolastatin10, Auristatin E, Auristatin PHE, and Maitansine based compounds (such as DM1 and DM4). Optionally, the recombinant bi-functional fusion protein (or the helper antibody) may further conjugated with a toxin, such as diphtheria toxin, *Pseudomonas aeruginosa* exotoxin A, ricin-chain A, abrin-chain A, volkensin-chain A, alpha-sarcin, an aleuritesfordii protein, dianthin, and a phytolacca toxin from *Phytolaca Americana*. The recombinant bi-functional fusion protein (or the helper antibody) may optionally conjugated with one or more radioactive isotopes selected from the group consisting of $^{225}Ac$, $^{211}At$, $^{212}Bi$, $^{213}Bi$, $^{186}Rh$, $^{188}Rh$, $^{177}Lu$, $^{90}Y$, $^{131}I$, $^{67}Cu$, $^{125}I$, $^{123}I$, $^{77}Br$, $^{153}Sm$, $^{166}Ho$, $^{64}Cu$, $^{121}Pb$, $^{224}Ra$ and $^{223}Ra$. Therefore, the present disclosure comprises a recombinant bi-functional fusion protein present as an antibody-drug conjugate (ADC) or an antibody-radioisotope conjugate (ARC).

Pharmaceutical Composition and Administration

The present disclosure further provides a composition. In a preferable embodiment, the composition is a pharmaceutical composition, containing the antibody or a functional fragment thereof or a fusion protein thereof described above, or the recombinant bi-functional fusion protein mentioned above, and a pharmaceutically acceptable carrier. Generally, these ingredients can be formulated in a nontoxic, nonreactive and pharmaceutically acceptable aqueous vehicle, normally with a pH of about 5 to 8, preferably a pH of about 6 to 8, although the pH may change depending on the ingredient properties and the diseases to be treated. The well prepared pharmaceutical composition may be administered by conventional administration routes, including, but not limited to, intra-tumor, intraperitoneal, intravenous, and topical administrations.

The pharmaceutical composition of the present disclosure may be used to prevent and treat tumors. Other therapeutic agents may be used in combination.

The pharmaceutical composition of the present disclosure contains an safe and effective amount (e.g., 0.001-99 wt %, preferably 0.01-90 wt %, more preferably 0.1-80 wt %) of the binding molecule (or its conjugate) mentioned above and a pharmaceutically acceptable carrier or excipient. The carrier includes, but not limited to, saline, a buffering solution, glucose, water, glycerol, ethanol, and the combination thereof. The pharmaceutical preparation has to match the administration route. The pharmaceutical composition of the present disclosure may be prepared as a parenteral preparation formulated by conventional methods using physiological saline or an aqueous solution containing glucose and other inactive ingredients. The pharmaceutical composition such as a parenteral preparation or a solution preparation may be formulated under sterile conditions. The active ingredient is to be administered in a therapeutically effective amount, such as about 1 microgram/kilogram body weight to about 5 milligram/kilogram body weight per day. The polypeptide of the present disclosure may be administered with additional therapeutic agents.

Upon administering the pharmaceutical composition, a safe and effective amount of the immunoconjugate is administered to a mammal. The safe and effective amount is generally at least about 10 microgram/kilogram body weight, and in most cases no higher than about 8 milligram/kilogram body weight, and preferably ranges from about 10 microgram/kilogram body weight to about 1 milligram/kilogram body weight. The dose may be specified in consideration of the administration route, the patient's conditions and etc., which can be handled by a skilled physician.

Materials and Methods

1. Construction of Vectors Expressing CD20mAb-SD1 or SD1-CD20mAb and Protein Expression A sequence encoding CD20mAb-H-SD1 or SD1-CD20mAb-H was obtained by linking a sequence coding for the first extracellular domain of human SIRPα(SIRPα-domain 1, SD1) to 5' or 3' end of a Rituximab heavy chain-encoding sequence and then adding two restriction sites (HindIII at 5' end and SalI at 3' end) at both ends. The sequences coding for CD20mAb-H-SD1, SD1-CD20mAb-H and Rituximab' light chain (CD20mAb-L) were synthesized in Suzhou Shengxin Biotech Co., Ltd, and inserted into pMac-H and pMac-L expression vectors (Macroimmune Inc.) to obtain expression vectors pMac-CD20mAb-H-SD1, pMac-SD1-CD20mAb-H and pMac-CD20mAb-L.

The vector pMac-CD20mAb-H-SD1 or pMac-SD1-CD20mAb-H co-infected CHO cells (purchased from ATCC) with pMac-CD20mAb-L. The cells were subject to several rounds of pressure selection to obtain CHO cells stably expressing CD20mAb-SD1 or SD1-CD20mAb. The cells were cultured in a larger scale to prepare 500 mg of CD20mAb-SD1 or SD1-CD20mAb proteins.

2. SEC-HPLC Analysis

One milligram of CD20mAb-SD1 or SD1-CD20mAb was subject to SEC-HPLC analysis.

3. Target Binding Activity (FACS)

Two tumor cell lines were used to test CD20mAb-SD1 and SD1-CD20mAb's binding activities to CD20 and CD47 in comparison to a single target-binding protein. In specific, Jurkat cells ($CD20^-CD47^+$) were used in CD47 binding test, while Raji-CD47KO cells ($CD20^+CD47^-$) was for CD20 binding test.

4. CD47 Binding in Competitive Assay (FACS)

Serially diluted CD20mAb-SD1, SD1-CD20mAb, SIRPα-Fc (as a positive control) and Rituximab were mixed with 25 nM biotin labeled SIRPα-Fc (biotin-SIRPα-Fc), respectively. The mixture was cultured at RT for 30 minutes, and then incubated with Jurkat cells at RT for 1 hour. After washes, the cells was added with fluorescence labeled streptavidin (FITC-Strep) and then incubated at RT for 1 hour. The cells were washed, suspended in 100 μL of cold phosphate buffer saline (PBS), and injected into a flow cytometer for analyzing the binding of SIRPα-Fc to cells by FACS.

5. ADCC

Raji cells or CD47 knockout Raji cells (Raji-CD47KO), $10^6$/ml, the target cells, were mixed with 1 mM CFSE (1:500) and incubated at 37° C. for 30 min, shaken every 10 min for better blending. NK92MI-CD16a cells, the effector cells, having a density of $6\times10^5$/ml, were mixed with the target cells at a 2:1 ratio. These cells were added with serially diluted CD20mAb-SD1, SD1-CD20mAb, Rituximab (as a positive control) and Herceptin/Trastuzumab (as a negative control), respectively, and incubated for 4 hours in a 37° C. and 5% $CO_2$ incubator. After incubation, the plate containing cells was kept still at RT for 10 min to cool the culture down to RT, and each cell of the plate was added with 20 μl of propodium iodide (PI) at a final concentration of 5 μg/ml. Then, the cells were subject to FACS analysis to determine the % PI positive cell at each protein concentration and accordingly the ADCC activity using the following formula.

% Lysis=(% PI positive cells in a group with protein/antibody treatment−% PI positive cells in a group without protein/antibody treatment)/ (100−% PI positive cells in a group without protein/antibody treatment)*100

The Lysis % was plotted against protein concentration using GraphPad Prism.

6. CDC

In a first test, Raji cells (as target cells) were mixed with serially diluted CD20mAb-SD1, Rituximab (as a positive control) and Herceptin (as a negative control), respectively. In a second test, Raji cells (as target cells) were mixed with serially diluted CD20mAb-SD1 and SD1-CD20mAb, respectively. Then, the mixture was added with rabbit complement at a certain concentration, and the cells were incubated for 4 hours in a 37° C. and 5% $CO_2$ incubator. After incubation, the plate containing cells was kept still at RT for 10 min to cool the culture down to RT, and each cell of the plate was added with 20 μl of propodium iodide (PI) at a final concentration of 5 μg/ml. Then, the cells were subject to FACS analysis to determine the % PI positive cell at each protein concentration and accordingly the CDC activity using the following formula.

Lysis %=Lysis % in a group with protein/antibody treatment−lysis % in a group without protein/antibody treatment The Lysis % was plotted against protein concentration using GraphPad Prism.

7. Phagocytosis

Mouse macrophage cell line Ana-1 was seeded in a 96-well cell culture plate, $1\times10^5$ cells per well, and cultured for 16-18 hours in a 37° C. and 5% $CO_2$ incubator. Target cells (HL-60) were labeled with CFSE, and then incubated with serially diluted CD20mAb-SD1, SD1-CD20mAb, SIRPα-Fc (as a positive control) and Rituximab (as a negative control) for 45 minutes at 37° C. and 5% $CO_2$. The target cell solutions with the test proteins were transferred to the plate containing Ana-1 cells. The mixture was cultured for 2 hours at 37° C. and 5% $CO_2$ and then washed to remove unbound target cells. The macrophages were collected and subject to FACS analysis for CFSE intensity.

8. In Vivo Anti-Tumor Test

In a first test, an in situ tumor model with Raji cells was used to investigate CD20mAb-SD1's in vivo anti-tumor activity. Thirty nude mice were injected at the caudal vein with Raji cells, $5×10^6$ cells per mouse. The next day, they were randomly allocated into five groups, and the mice in Groups 1 to 5 were intraperitoneally administered with PBS, CD20mAb-SD1 (5 mg/kg), SD1-Fc (2.5 mg/kg), Rituximab (2.5 mg/kg), and SD1-Fc plus Rituximab (2.5+2.5 mg/kg), respectively, once a week, with a total of five injections. Mice were observed for their physical conditions and measured for body weights every day.

In a second test, a subcutaneous tumor model with Raji cells was used to investigate CD20mAb-SD1 and SD1-CD20mAb's in vivo anti-tumor activities. Forty nude mice were subcutaneously injected with Raji cells, $6×10^6$ cells per mouse. When the tumor volume reached about 120 $mm^3$, these mice were randomly allocated into five groups, 8 mice per group. The mice in Groups 1 to 5 were intraperitoneally administered with PBS, Rituximab with enhanced ADCC activity (Rituximab-ADCC+) (2.5 mg/kg), CD20mAb-SD1 (5 mg/kg), SD1-CD20mAb (5 mg/kg), and Rituximab plus SIRPαD1-Fc (3+3 mg/kg), respectively, once a week, with a total of five injections. Tumor volume and body weight were measured twice a week, and the physical conditions were observed and recorded every day. At day 28, mice were sacrificed after completion of measurement, and tumors were removed, weighted and photographed.

The present disclosure has the following advantages, among others:

(1) The recombinant bi-functional fusion proteins (CD20mAb-SD1 and SD1-CD20mAb) designed in the present disclosure have evident anti-tumor activities, which are much better than that provided by Rituximab alone, or the combination of two single target-binding drugs (Rituximab plus SIRPαD1-Fc);

(2) The recombinant bi-functional fusion protein SD1-CD20mAb of the present disclosure has much better anti-tumor activity than CD20mAb-SD1;

(3) The recombinant bi-functional fusion proteins of the present disclosure, CD20mAb-SD1 and SD1-CD20mAb, may be used to treat patients insensitive or tolerant to Rituximab.

The present disclosure will be described in further detail with the following examples. It should be understood that these examples are used to illustrate the present disclosure but not to limit the present disclosure. The methods in the examples that are not described with specified protocols were performed using conventional protocols described in e.g., Sambrook et al., Molecular Coning: A Laboratory Manual, New York: Cold Spring Harbor Laboratory Press, 1989, or following the manufacture's manual. Unless otherwise specified, the percent or part refers to weight percent or weight part, and the materials and reagents used in the examples were commercially available.

Example 1. Construction of Vectors Expressing CD20mAb-SD1 and SD1-CD20mAb

Figure 2:
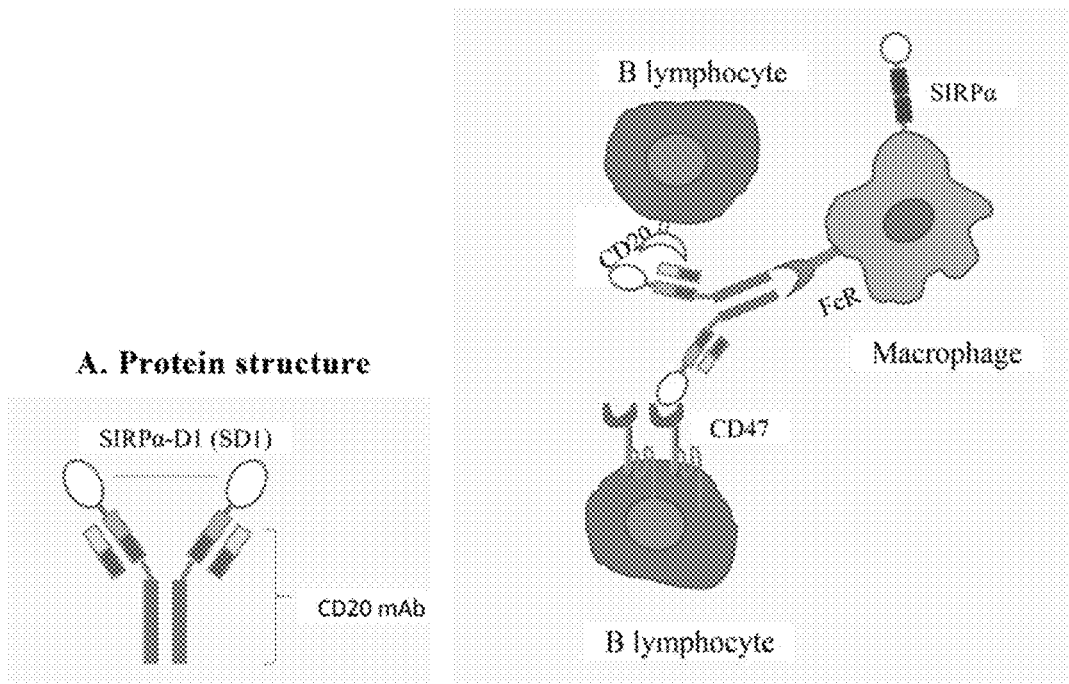
FIG. 2 shows the structure and action mechanisms of SD1-CD20mAb.

CD20mAb-SD1 and SD1-CD20mAb's structures were shown in FIG. 1 and FIG. 2, either composed of four chains (two heavy chains and two light chains) connected by corresponding disulfide bonds, wherein the heavy chains and light chains were encoded by a heavy chain coding sequence and a light chain coding sequence, respectively. The heavy chain coding sequence of CD20mAb-SD1 consisted of 1749 nucleotides (FIG. 3A), wherein 1350 nucleotides encoded the CD20mAb heavy chain of 450 amino acid residues (1-450), and 399 nucleotides encoded SD1 of 133 amino acid residues (451-583). The corresponding amino acid sequence was shown in FIG. 4A. The heavy chain coding sequence of SD1-CD20mAb consisted of 1782 nucleotides (FIG. 3C), wherein 399 nucleotides encoded SD1 of 133 amino acid residues (1-133), 30 nucleotides encoded a linker peptide of 10 amino acid residues (134-143), and 1353 nucleotides encoded the CD20mAb heavy chain of 451 amino acid residues (144-597). The corresponding amino acid sequence was shown in FIG. 4C. Both CD20mAb-SD 1 and SD1-CD20mAb contained a light chain of 213 amino acid residues (1-213) (FIG. 4B and FIG. 4D), encoded by 639 nucleotides (FIG. 3B and FIG. 3D).

Example 2. SEC-HPLC Analysis

Figure 5A:
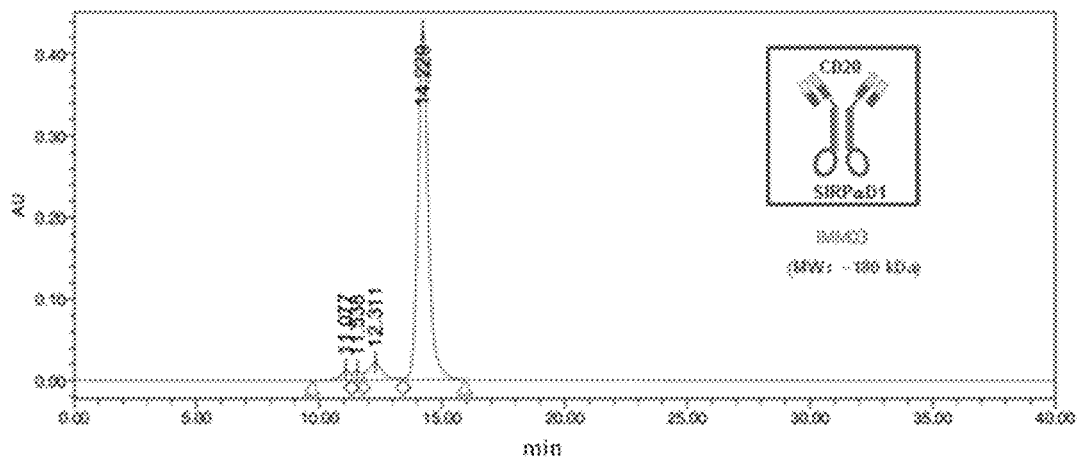
FIGS. 5A and 5B show the SEC-HPLC analysis results, with the SEC-HPLC analysis result of CD20mAb-SD1 in FIG. 5A, and the SEC-HPLC analysis result of SD1-CD20mAb in FIG. 5B.
Figure 5B:
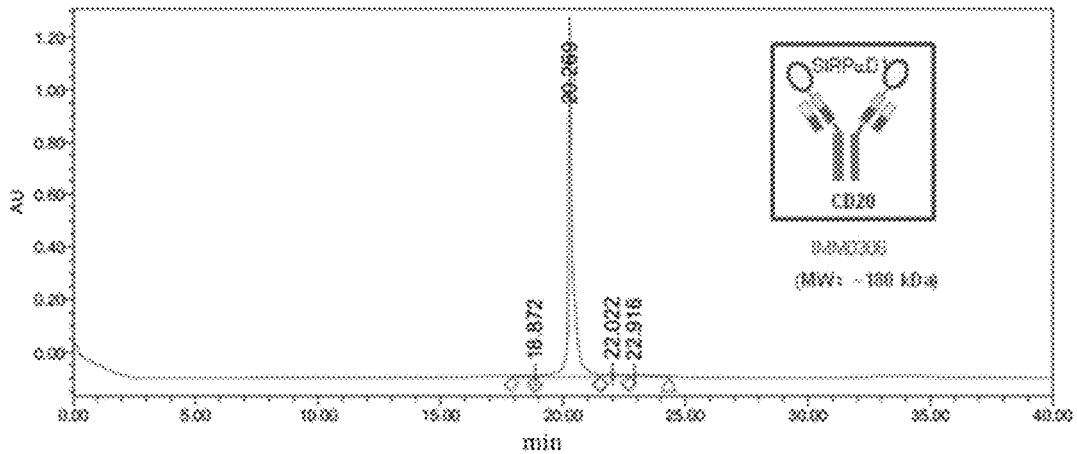
Figure 6:
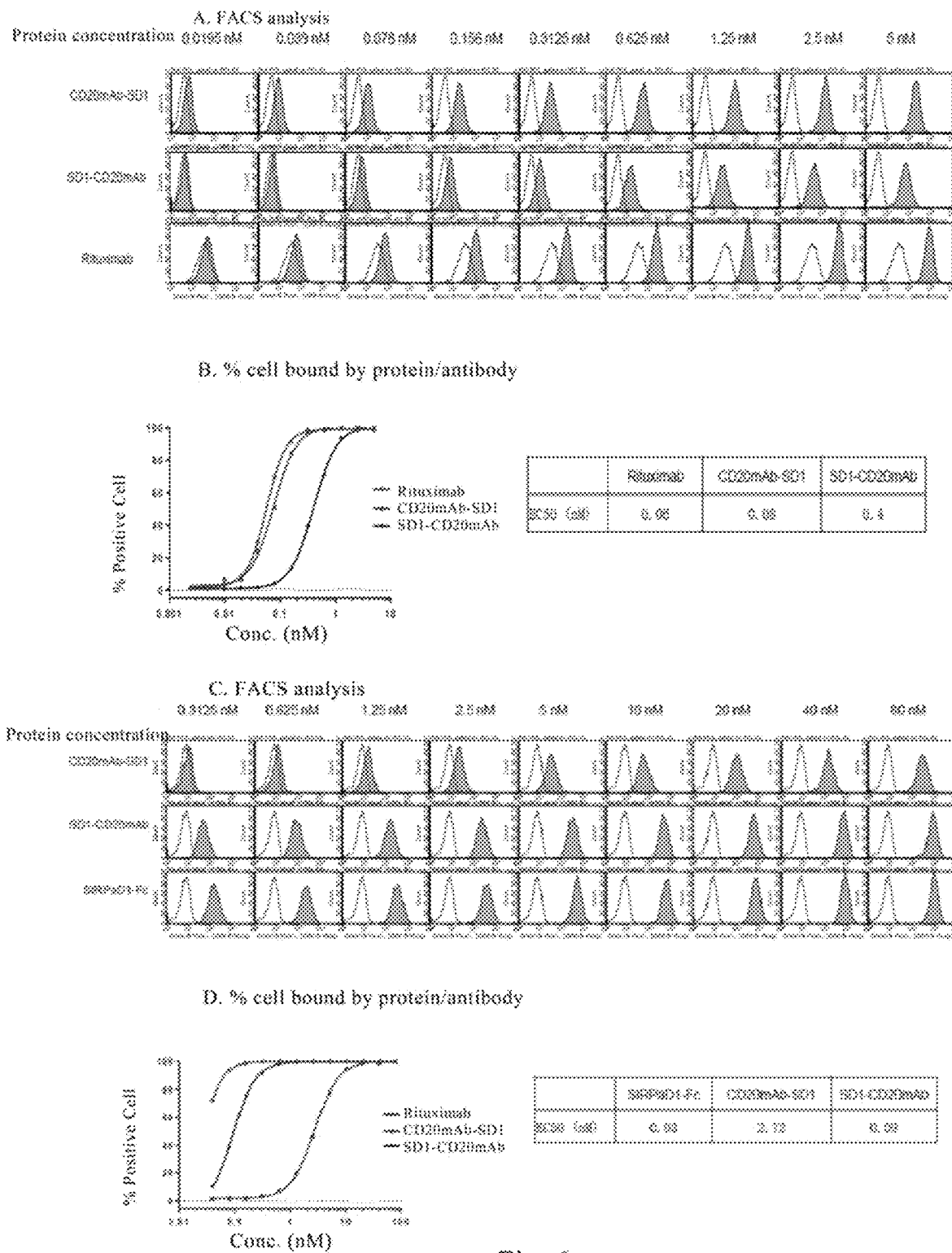
FIG. 6 shows the recombinant proteins' binding activities to targets, with the recombinant proteins' binding activities to CD20 in Panels A and B, and the recombinant proteins' binding activities to CD47 in Panels C and D.

It was confirmed in the SEC-HPLC test that both CD20mAb-SD1 and SD1-CD20mAb had very good protein integrity, with peptide fragments of low molecular weights accounting for 1 to 3%, and there was less than 3% of protein polymers (FIGS. 5A and 5B).

Example 3. Target Binding Capacities

The binding capacities of CD20mAb-SD1 and SD1-CD20mAb to CD20 and CD47 were tested using a flow cytometer. The results showed that both proteins had high binding capacities to both targets, having $EC_{50}$ at the nmol level. In specific, CD20mAb-SD1's binding capacity to CD20 was similar to that of Rituximab, and the $EC_{50}$ of the two were 0.08 nM and 0.06 nM, respectively. SD1-CD20mAb's binding capacity was a bit lower, with EC50 of 0.4 nM. SD1-CD20mAb had a much better binding capacity to CD47 than CD20mAb-SD1, the EC50 of the two were 0.09 nM and 2.72 nM, respectively.

Example 4. CD47 Binding in Competitive Assay

Using Jurkat cells, CD20mAb-SD1 and SD1-CD20mAb were tested for their binding activities to CD47 over SIRPα. As shown in FIG. 7, both proteins significantly inhibited the binding of SIRPαs to Jurkat cells, and SD1-CD20mAb's inhibitory effect was significantly better than CD20mAb-SD1's, the EC50 of the two were 19.74 nM and 476.2 nM, respectively.

Example 5. ADCC and CDC Activities

Both CD20mAb-SD1 and SD1-CD20mAb had ADCC (FIGS. 8A and 8B) and CDC (FIGS. 8C and 8D) activities. In specific, these two proteins had similar ADCC activities which were significantly superior to that of Rituximab. When Raji cells were used as the target cells, the EC50 of CD20mAb-SD1, SD1-CD20mAb and Rituximab were 0.14 ng/ml, 0.15 ng/ml and 3.82 ng/ml, respectively. For Raji-CD47KO cells, the EC50 of CD20mAb-SD1, SD1-CD20mAb and Rituximab were 0.14 ng/ml, 0.10 ng/ml and 1.13 ng/ml, respectively. Further, both proteins showed promising CDC activities, with SD1-CD20mAb's CDC (EC50=3.36 nM) much better than CD20mAb-SD1's (EC50=10.97 nM).

Example 6. Phagocytosis by Macrophages

Figure 9:
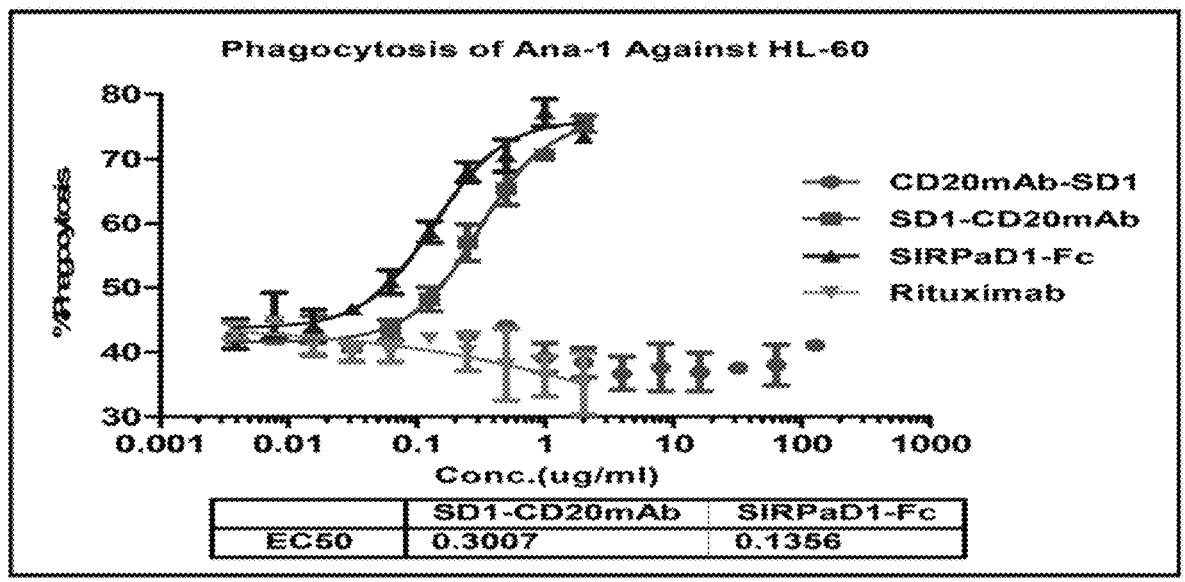
FIG. 9 shows the recombinant proteins' capacities of inducing macrophage phagocytosis.
Figure 10A:
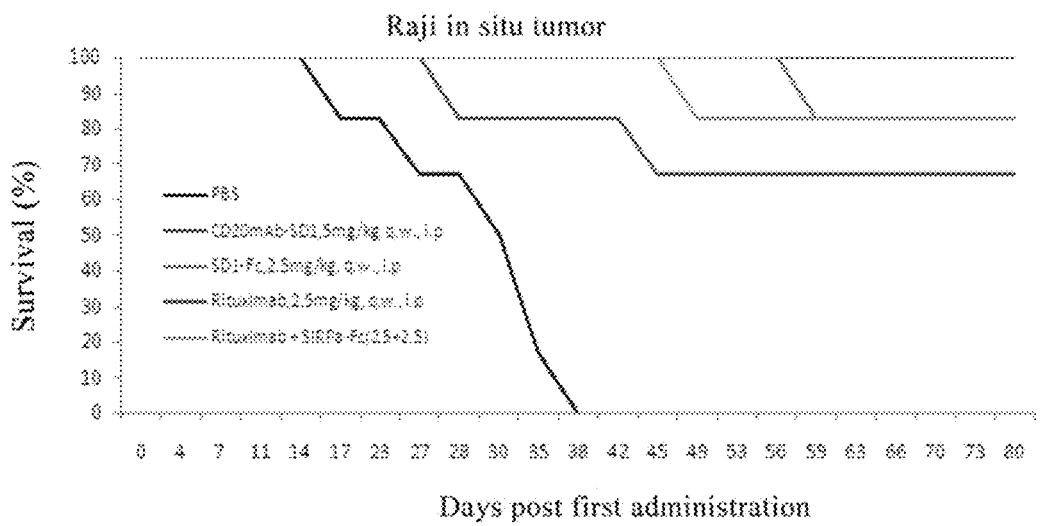
FIG. 10 shows the recombinant proteins' in vivo anti-tumor activities, with CD20mAb-SD1's in vivo anti-tumor activity in FIG. 10A, and the CD20mAb-SD1 and SD1-CD20mAb's in vivo anti-tumor activities in FIG. 10B.
Figure 10B:
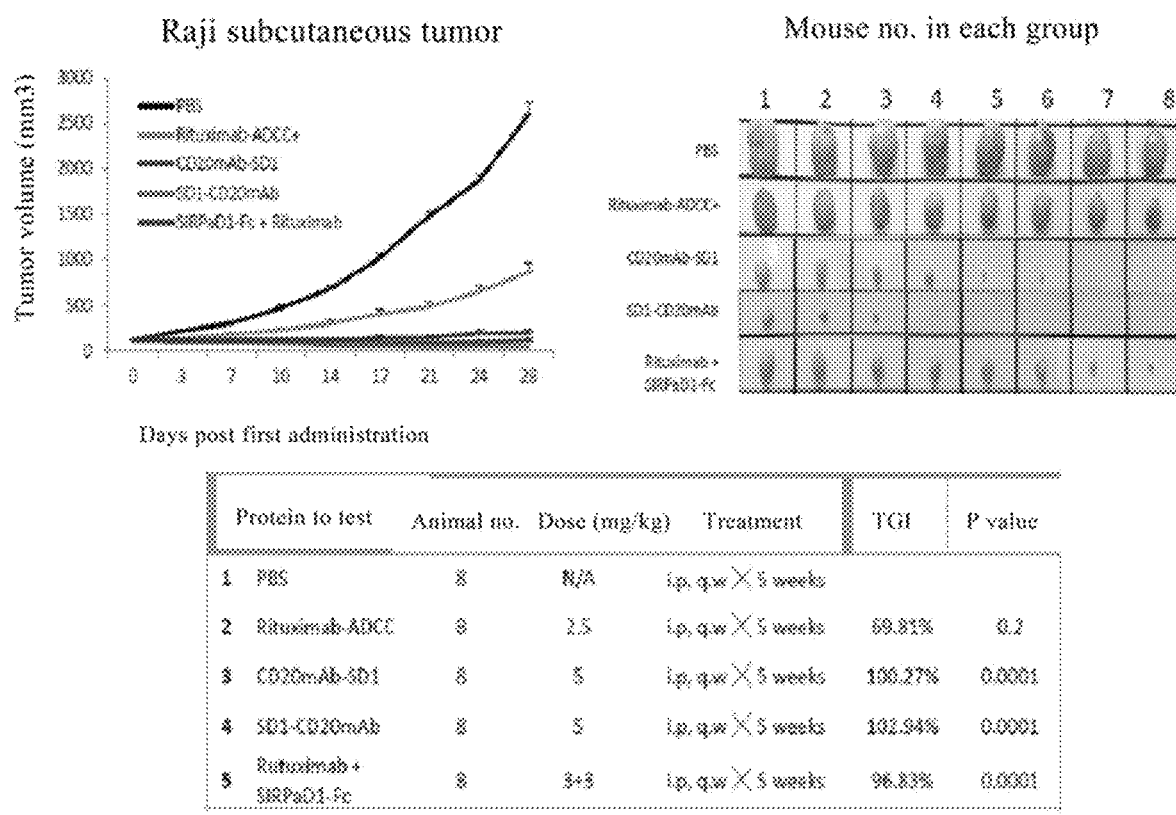

CD20mAb-SD1 and SD1-CD20mAb's roles in promoting phagocytosis of tumor cells by macrophages were tested using mouse macrophage cell line Ana-1. As shown in FIG. 9, SD1-CD20mAb (EC50=0.3 μg/ml) induced phagocytosis at a similar level as compared to SIRPαD1-Fc (EC50=0.14 μg/ml), while CD20mAb-SD1 did not induce macrophage phagocytosis.

Example 7. In Vivo Anti-Tumor Activity

CD20mAb-SD1's in vivo anti-tumor activity was studied using an in situ tumor model with Raji cells. As shown in FIG. 10A, all mice from the group without any protein/antibody treatment died in no more than 38 days since they began to receive drug administrations. In the groups administered with single target-binding proteins/antibodies, i.e., Rituximab and SIRPαD1-Fc, more mice survived. Till the end of the test, the survival rates in these two groups were 67% and 83%, respectively. While in the CD20mAb-SD1 treatment group, 100% mice survived, suggesting CD20mAb-SD1's significantly better anti-tumor effect than the single target-binding proteins/antibodies.

Further, CD20mAb-SD1 and SD1-CD20mAb's in vivo anti-tumor activities were tested in a subcutaneous tumor model with Raji cells. As shown in FIG. 10B, the mice from the group without protein/antibody treatment had their tumors rapidly grow with increasing tumor volumes, and the tumors were about 2500 $mm^3$ in size at the end of the test. On the other hand, the tumors grew slowly in the mice treated with CD20mAb-SD1 or SD1-CD20mAb, and the average tumor volume even decreased. Till the end of the test, the average tumor sizes in these two groups were both smaller than those at the beginning of the test. More surprisingly, among 8 mice administered with SD1-CD20mAb, 5 had their tumors vanished. In the group with CD20mAb-SD1 administration, 2 out of 8 mice had their tumors completely gone. These suggested that SD1-CD20mAb's in vivo anti-tumor activity was superior to that of CD20mAb-SD1. When Rituximab was administered in combination with SIRPαD1-Fc, the anti-tumor effect was not as good as that achieved by CD20mAb-SD1 or SD1-CD20mAb (upper right panel, FIG. 10B).

The studies in the present disclosure suggested that the recombinant bi-functional proteins CD20mAb-SD1 and SD1-CD20mAb were novel fusion proteins having high two-target-binding activities. The tests showed such proteins were capable of inducing ADCC and CDC and blocking SIRPαD1-Fc-CD47 interaction, and can be used in treatment of CD20+CD47+ cancers.

All publications mentioned in the present application are herein incorporated for reference, as if each and every of them is solely cited for reference. Further, in view of the disclosures above, various modifications and variations of the described proteins and methods will be apparent to those skilled in the art without departing from the scope and spirit of the present disclosure.

We claim:

1. A recombinant bi-functional fusion protein, comprising an antibody specifically binding to CD20, wherein the protein comprises an antibody selected from the group consisting of Rituximab, Obinutuzumab, and Ofatumumab, and a peptide derived from SIRPα comprising SEQ ID NO: 9.

2. A recombinant bi-functional fusion protein, comprising an antibody specifically binding to CD20, wherein the protein comprises a heavy chain variable region of SEQ ID NO: 5, a light chain variable region of SEQ ID NO: 7, and a peptide derived from SIRPα comprising SEQ ID NO: 9.

3. The recombinant bi-functional fusion protein according to claim 1, wherein the antibody contains a heavy chain and a light chain, and the peptide is linked to the N-terminus of the heavy chain of the antibody.

4. The recombinant bi-functional fusion protein according to claim 1, wherein the antibody contains a heavy chain and a light chain, and the peptide is linked to the C-terminus of the heavy chain of the antibody.

5. An immunoconjugate containing
   (a) the recombinant bi-functional fusion protein according to claim 1, and
   (b) a second molecule conjugated to the recombinant bi-functional fusion protein selected from the group consisting of a detectable marker, a drug, a toxin, a cytokine, a radionuclide, and an enzyme.

6. A pharmaceutical composition containing:
   (i) the recombinant bi-functional fusion protein according to claim 1, or the immunoconjugate according to claim 5, and
   (ii) a pharmaceutically acceptable carrier.

7. A method for treating a CD20+ tumor, comprising administering to a subject in need thereof a therapeutically effective amount of the pharmaceutical composition according to claim 6.

8. The method according to claim 7, wherein the tumor is selected from the group consisting of stomach cancer, liver cancer, leukemia, kidney tumor, lung cancer, small intestinal cancer, bone cancer, prostatic cancer, colorectal cancer, breast cancer, large intestinal cancer, prostatic cancer, cervical cancer, adrenal cancer, and bladder cancer.

* * * * *

SEQUENCE LISTING

```
<160> NUMBER OF SEQ ID NOS: 13

<210> SEQ ID NO 1
<211> LENGTH: 1752
<212> TYPE: DNA
<213> ORGANISM: Artificial Sequence
<220> FEATURE:
<223> OTHER INFORMATION: heavy chain-SD1

<400> SEQUENCE: 1
caggtccagc tgcagcagcc gggcgcggag ctcgtgaagc cgggggcctc ggtcaagatg     60
agctgcaagg ccagcggcta caccttcacg agctacaaca tgcactgggt gaagcagacc    120
ccgggccggg ggctggagtg gatcggcgcc atctaccccg ggaacggcga caccagctac    180
aaccagaagt tcaagggcaa ggcgaccctg acggcggaca agtcgagcag caccgcctac    240
atgcagctca gcagcctgac ctcggaggac agcgccgtct actactgcgc ccggtccacg    300
tactacggcg gcgactggta cttcaacgtc tgggggggccg gcacgaccgt gaccgtgagc    360
gcggctagca ccaagggccc atcggtcttc cccctggcac cctcctccaa gagcacctct    420
gggggcacag cggccctggg ctgcctggtc aaggactact tccccgaacc ggtgacggtg    480
tcgtggaact caggcgccct gaccagcggc gtgcacacct tcccggctgt cctacagtcc    540
tcaggactct actccctcag cagcgtggtg accgtgccct ccagcagctt gggcacccag    600
acctacatct gcaacgtgaa tcacaagccc agcaacacca aggtggacaa gagagttgag    660
cccaaatctt gtgacaaaac tcacacatgc ccaccgtgcc cagcacctga actcctgggg    720
ggaccgtcag tcttcctctt ccccccaaaa cccaaggaca ccctcatgat ctcccggacc    780
cctgaggtca catgcgtggt ggtggacgtg agccacgaag accctgaggt caagttcaac    840
```

```
tggtatgtgg acggcgtgga ggtgcataat gccaagacaa agccgcggga ggagcagtac      900
aacgccacgt accgtgtggt cagcgtcctc accgtcctgc accaagactg gctgaatggc      960
aaggagtaca agtgcaaggt ctccaacaaa gccctcccag cccccatcgc cgcaaccatc     1020
tccaaagcca aagggcagcc ccgagaacca caggtgtaca ccctgccccc atcccgggag     1080
gagatgacca agaaccaagt cagcctgacc tgcctggtca aaggcttcta tcccagcgac     1140
atcgccgtgg agtgggagag caatgggcag ccggagaaca actacaagac cacgcctccc     1200
gtgctggact ccgacggctc cttcttcctc tattccaagc tcaccgtgga caagagcagg     1260
tggcagcagg ggaacgtctt ctcatgctcc gtgatgcatg aggctctgca caaccactac     1320
acgcagaaga gcctctccct gtctccgggc gaggaggagc tgcaggtgat tcagcctgac     1380
aagtccgtat cagttgcagc tggagagtcg gccattctgc actgcactgt gacctccctg     1440
atccctgtgg ggcccatcca gtggttcaga ggagctggac cagcccggga attaatctac     1500
aatcaaaaag aaggccactt cccccgggta acaactgttt cagagtccac aaagagagaa     1560
aacatggact tttccatcag catcagtgcc atcaccccag cagatgccgg cacctactac     1620
tgtgtgaagt tccggaaagg gagccctgac acggagttta agtctggagc aggcactgag     1680
ctgtctgtgc gtgccaaacc ctctgccccc gtggtatcgg gccctgcggc gagggccaca     1740
cctcagcact ga                                                        1752

<210> SEQ ID NO 2
<211> LENGTH: 642
<212> TYPE: DNA
<213> ORGANISM: Artificial Sequence
<220> FEATURE:
<223> OTHER INFORMATION: light chain

<400> SEQUENCE: 2
cagatcgtgc tgagccagtc gccggccatc ctcagcgcga gccccggcga aaggtcacc       60 atgacgtgcc gggccagcag ctcggtgagc tacatccact ggttccagca aaagcccggg      120
agcagcccca gccgtggat ctacgccacc agcaacctgg cctcgggcgt gcccgtgcgc      180
ttcagcggga gcggcagcgg gaccagctac agcctgacca tctcgcgggt cgaggccgag      240
gacgccgcca cctactactg ccagcagtgg acctccaacc cgcccacgtt cggcggcggc      300
accaagcacg agctgaagcg aactgtggct gcaccatctg tcttcatctt cccgccatct      360
gatgagcagt tgaaatctgg aactgcctct gttgtgtgcc tgctgaataa cttctatccc      420
agagaggcca aagtacagtg gaaggtggat aacgccctcc aatcgggtaa ctcccaggag      480
agtgtcacag agcaggacag caaggacagc acctacagcc tcagcagcac cctgacgctg      540
agcaaagcag actacgagaa acacaaagtc tacgcctgcg aagtcaccca tcagggcctg      600
agctcgcccg tcacaaagag cttcaacagg ggagagtgtt ag                        642

<210> SEQ ID NO 3
<211> LENGTH: 583
<212> TYPE: PRT
<213> ORGANISM: Artificial Sequence
<220> FEATURE:
<223> OTHER INFORMATION: heavy chain-SD1

<400> SEQUENCE: 3

Gln Val Gln Leu Gln Gln Pro Gly Ala Glu Leu Val Lys Pro Gly Ala
1               5                   10                  15

Ser Val Lys Met Ser Cys Lys Ala Ser Gly Tyr Thr Phe Thr Ser Tyr
```

-continued

```
            20                  25                  30
Asn Met His Trp Val Lys Gln Thr Pro Gly Arg Gly Leu Glu Trp Ile
         35                  40                  45
Gly Ala Ile Tyr Pro Gly Asn Gly Asp Thr Ser Tyr Asn Gln Lys Phe
 50                  55                  60
Lys Gly Lys Ala Thr Leu Thr Ala Asp Lys Ser Ser Thr Ala Tyr
 65                  70                  75                  80
Met Gln Leu Ser Ser Leu Thr Ser Glu Asp Ser Ala Val Tyr Tyr Cys
             85                  90                  95
Ala Arg Ser Thr Tyr Tyr Gly Gly Asp Trp Tyr Phe Asn Val Trp Gly
                100                 105                 110
Ala Gly Thr Thr Val Thr Val Ser Ala Ala Ser Thr Lys Gly Pro Ser
            115                 120                 125
Val Phe Pro Leu Ala Pro Ser Ser Lys Ser Thr Ser Gly Gly Thr Ala
        130                 135                 140
Ala Leu Gly Cys Leu Val Lys Asp Tyr Phe Pro Glu Pro Val Thr Val
145                 150                 155                 160
Ser Trp Asn Ser Gly Ala Leu Thr Ser Gly Val His Thr Phe Pro Ala
                165                 170                 175
Val Leu Gln Ser Ser Gly Leu Tyr Ser Leu Ser Ser Val Val Thr Val
            180                 185                 190
Pro Ser Ser Ser Leu Gly Thr Gln Thr Tyr Ile Cys Asn Val Asn His
        195                 200                 205
Lys Pro Ser Asn Thr Lys Val Asp Lys Arg Val Glu Pro Lys Ser Cys
    210                 215                 220
Asp Lys Thr His Thr Cys Pro Pro Cys Pro Ala Pro Glu Leu Leu Gly
225                 230                 235                 240
Gly Pro Ser Val Phe Leu Phe Pro Pro Lys Pro Lys Asp Thr Leu Met
                245                 250                 255
Ile Ser Arg Thr Pro Glu Val Thr Cys Val Val Val Asp Val Ser His
            260                 265                 270
Glu Asp Pro Glu Val Lys Phe Asn Trp Tyr Val Asp Gly Val Glu Val
        275                 280                 285
His Asn Ala Lys Thr Lys Pro Arg Glu Glu Gln Tyr Asn Ala Thr Tyr
    290                 295                 300
Arg Val Val Ser Val Leu Thr Val Leu His Gln Asp Trp Leu Asn Gly
305                 310                 315                 320
Lys Glu Tyr Lys Cys Lys Val Ser Asn Lys Ala Leu Pro Ala Pro Ile
                325                 330                 335
Ala Ala Thr Ile Ser Lys Ala Lys Gly Gln Pro Arg Glu Pro Gln Val
            340                 345                 350
Tyr Thr Leu Pro Pro Ser Arg Glu Glu Met Thr Lys Asn Gln Val Ser
        355                 360                 365
Leu Thr Cys Leu Val Lys Gly Phe Tyr Pro Ser Asp Ile Ala Val Glu
    370                 375                 380
Trp Glu Ser Asn Gly Gln Pro Glu Asn Asn Tyr Lys Thr Thr Pro Pro
385                 390                 395                 400
Val Leu Asp Ser Asp Gly Ser Phe Phe Leu Tyr Ser Lys Leu Thr Val
                405                 410                 415
Asp Lys Ser Arg Trp Gln Gln Gly Asn Val Phe Ser Cys Ser Val Met
            420                 425                 430
His Glu Ala Leu His Asn His Tyr Thr Gln Lys Ser Leu Ser Leu Ser
        435                 440                 445
```

```
Pro Gly Glu Glu Glu Leu Gln Val Ile Gln Pro Asp Lys Ser Val Ser
    450                 455                 460
Val Ala Ala Gly Glu Ser Ala Ile Leu His Cys Thr Val Thr Ser Leu
465                 470                 475                 480
Ile Pro Val Gly Pro Ile Gln Trp Phe Arg Gly Ala Gly Pro Ala Arg
                485                 490                 495
Glu Leu Ile Tyr Asn Gln Lys Glu Gly His Phe Pro Arg Val Thr Thr
            500                 505                 510
Val Ser Glu Ser Thr Lys Arg Glu Asn Met Asp Phe Ser Ile Ser Ile
            515                 520                 525
Ser Ala Ile Thr Pro Ala Asp Ala Gly Thr Tyr Tyr Cys Val Lys Phe
            530                 535                 540
Arg Lys Gly Ser Pro Asp Thr Glu Phe Lys Ser Gly Ala Gly Thr Glu
545                 550                 555                 560
Leu Ser Val Arg Ala Lys Pro Ser Ala Pro Val Val Ser Gly Pro Ala
                565                 570                 575
Ala Arg Ala Thr Pro Gln His
            580
```

```
<210> SEQ ID NO 4
<211> LENGTH: 213
<212> TYPE: PRT
<213> ORGANISM: Artificial Sequence
<220> FEATURE:
<223> OTHER INFORMATION: light chain

<400> SEQUENCE: 4

Gln Ile Val Leu Ser Gln Ser Pro Ala Ile Leu Ser Ala Ser Pro Gly
1               5                   10                  15
Glu Lys Val Thr Met Thr Cys Arg Ala Ser Ser Ser Val Ser Tyr Ile
                20                  25                  30
His Trp Phe Gln Gln Lys Pro Gly Ser Ser Pro Lys Pro Trp Ile Tyr
            35                  40                  45
Ala Thr Ser Asn Leu Ala Ser Gly Val Pro Val Arg Phe Ser Gly Ser
        50                  55                  60
Gly Ser Gly Thr Ser Tyr Ser Leu Thr Ile Ser Arg Val Glu Ala Glu
65                  70                  75                  80
Asp Ala Ala Thr Tyr Tyr Cys Gln Gln Trp Thr Ser Asn Pro Pro Thr
                85                  90                  95
Phe Gly Gly Gly Thr Lys His Glu Leu Lys Arg Thr Val Ala Ala Pro
            100                 105                 110
Ser Val Phe Ile Phe Pro Pro Ser Asp Glu Gln Leu Lys Ser Gly Thr
        115                 120                 125
Ala Ser Val Val Cys Leu Leu Asn Asn Phe Tyr Pro Arg Glu Ala Lys
130                 135                 140
Val Gln Trp Lys Val Asp Asn Ala Leu Gln Ser Gly Asn Ser Gln Glu
145                 150                 155                 160
Ser Val Thr Glu Gln Asp Ser Lys Asp Ser Thr Tyr Ser Leu Ser Ser
                165                 170                 175
Thr Leu Thr Leu Ser Lys Ala Asp Tyr Glu Lys His Lys Val Tyr Ala
            180                 185                 190
Cys Glu Val Thr His Gln Gly Leu Ser Ser Pro Val Thr Lys Ser Phe
        195                 200                 205
Asn Arg Gly Glu Cys
        210
```

<210> SEQ ID NO 5
<211> LENGTH: 121
<212> TYPE: PRT
<213> ORGANISM: Artificial Sequence
<220> FEATURE:
<223> OTHER INFORMATION: VH

<400> SEQUENCE: 5

Gln Val Gln Leu Gln Gln Pro Gly Ala Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Asn Met His Trp Val Lys Gln Thr Pro Gly Arg Gly Leu Glu Trp Ile
        35                  40                  45

Gly Ala Ile Tyr Pro Gly Asn Gly Asp Thr Ser Tyr Asn Gln Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Ser Thr Tyr Tyr Gly Gly Asp Trp Tyr Phe Asn Val Trp Gly
            100                 105                 110

Ala Gly Thr Thr Val Thr Val Ser Ala
        115                 120

<210> SEQ ID NO 6
<211> LENGTH: 363
<212> TYPE: DNA
<213> ORGANISM: Artificial Sequence
<220> FEATURE:
<223> OTHER INFORMATION: VH

<400> SEQUENCE: 6
caggtccagc tgcagcagcc gggcgcggag ctcgtgaagc cgggggcctc ggtcaagatg      60
agctgcaagg ccagcggcta caccttcacg agctacaaca tgcactgggt gaagcagacc     120
ccgggccggg gctggagtg atcggcgcc atctaccccg gaacggcga caccagctac        180 aaccagaagt tcaagggcaa ggcgacctg acggcggaca gtcgagcag caccgcctac       240 atgcagctca gcagcctgac ctcggaggac agcgccgtct actactgcgc ccggtccacg     300
tactacggcg gcgactggta cttcaacgtc tggggggccg gcacgaccgt gaccgtgagc     360
gcg                                                                  363

<210> SEQ ID NO 7
<211> LENGTH: 106
<212> TYPE: PRT
<213> ORGANISM: Artificial Sequence
<220> FEATURE:
<223> OTHER INFORMATION: VL

<400> SEQUENCE: 7

Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Ser Val Ser Tyr Ile
            20                  25                  30

His Trp Phe Gln Gln Lys Pro Gly Ser Ser Pro Lys Pro Trp Ile Tyr
        35                  40                  45

Ala Thr Ser Asn Leu Ala Ser Gly Val Pro Val Arg Phe Ser Gly Ser

```
                    50                  55                  60

Gly Ser Gly Thr Ser Tyr Ser Leu Thr Ile Ser Arg Val Glu Ala Glu
 65                  70                  75                  80

Asp Ala Ala Thr Tyr Tyr Cys Gln Gln Trp Thr Ser Asn Pro Pro Thr
                 85                  90                  95

Phe Gly Gly Gly Thr Lys Leu Glu Ile Lys
            100                 105
```

<210> SEQ ID NO 8
<211> LENGTH: 318
<212> TYPE: DNA
<213> ORGANISM: Artificial Sequence
<220> FEATURE:
<223> OTHER INFORMATION: VL

<400> SEQUENCE: 8

```
cagatcgtgc tgagccagtc gccggccatc ctcagcgcga gccccggcga gaaggtcacc    60
atgacgtgcc gggccagcag ctcggtgagc tacatccact ggttccagca gaagcccggg   120
agcagcccca agccgtggat ctacgccacc agcaacctgg cctcgggcgt gcccgtgcgc   180
ttcagcggga gcggcagcgg gaccagctac agcctgacca tctcgcgggt cgaggccgag   240
gacgccgcca cctactactg ccagcagtgg acctccaacc cgcccacgtt cggcggcggc   300
accaagctcg agatcaag                                                  318
```

<210> SEQ ID NO 9
<211> LENGTH: 133
<212> TYPE: PRT
<213> ORGANISM: Artificial Sequence
<220> FEATURE:
<223> OTHER INFORMATION: SD1

<400> SEQUENCE: 9

```
Glu Glu Glu Leu Gln Val Ile Gln Pro Asp Lys Ser Val Ser Val Ala
  1               5                  10                  15

Ala Gly Glu Ser Ala Ile Leu His Cys Thr Val Thr Ser Leu Ile Pro
                 20                  25                  30

Val Gly Pro Ile Gln Trp Phe Arg Gly Ala Gly Pro Ala Arg Glu Leu
             35                  40                  45

Ile Tyr Asn Gln Lys Glu Gly His Phe Pro Arg Val Thr Thr Val Ser
 50                  55                  60

Glu Ser Thr Lys Arg Glu Asn Met Asp Phe Ser Ile Ser Ile Ser Ala
 65                  70                  75                  80

Ile Thr Pro Ala Asp Ala Gly Thr Tyr Tyr Cys Val Lys Phe Arg Lys
                 85                  90                  95

Gly Ser Pro Asp Thr Glu Phe Lys Ser Gly Ala Gly Thr Glu Leu Ser
            100                 105                 110

Val Arg Ala Lys Pro Ser Ala Pro Val Val Ser Gly Pro Ala Ala Arg
        115                 120                 125

Ala Thr Pro Gln His
        130
```

<210> SEQ ID NO 10
<211> LENGTH: 213
<212> TYPE: PRT
<213> ORGANISM: Artificial Sequence
<220> FEATURE:
<223> OTHER INFORMATION: light chain

<400> SEQUENCE: 10

```
Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Val Ser Tyr Ile
            20                  25                  30

His Trp Phe Gln Gln Lys Pro Gly Ser Ser Pro Lys Pro Trp Ile Tyr
        35                  40                  45

Ala Thr Ser Asn Leu Ala Ser Gly Val Pro Val Arg Phe Ser Gly Ser
    50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Thr Ser Asn Pro Pro Thr
                85                  90                  95

Phe Gly Gly Gly Thr Lys His Glu Leu Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 11
<211> LENGTH: 1785
<212> TYPE: DNA
<213> ORGANISM: Artificial Sequence
<220> FEATURE:
<223> OTHER INFORMATION: SD1-heavy chain

<400> SEQUENCE: 11
gaggaggagc tgcaggtgat tcagcctgac aagtccgtat cagttgcagc tggagagtcg      60
gccattctgc actgcactgt gacctccctg atccctgtgg ggcccatcca gtggttcaga     120
ggagctggac cagcccggga attaatctac aatcaaaaag aaggccactt ccccgggta     180 acaactgttt cagagtccac aaagagagaa acatggact tttccatcag catcagtgcc      240
atcaccccag cagatgccgg cacctactac tgtgtgaagt ccggaaaagg agccctgac      300 acggagttta agtctggagc aggcactgag ctgtctgtgc gtgccaaacc ctctgcccc      360 gtggtatcgg gccctgcggc gagggccaca cctcagcacg gcggcggtgg gagcggcggc     420
gggggctcgc aggtccagct gcagcagccg ggcgcggagc tcgtgaagcc gggggcctcg     480
gtcaagatga ctgcaaggc cagcggctac accttcacga gctacaacat gcactgggtg     540
aagcagaccc cggccggggg ctggagtgg atcggcgcca tctacccgg gaacggcgac     600 accagctaca accagaagtt caagggcaag gcgaccctga cggcggacaa gtcgagcagc     660
accgcctaca tgcagctcag cagcctgacc tcggaggaca cgccgtcta ctactgcgcc     720 cggtccacgt actacggcgg cgactggtac ttcaacgtct ggggggccgg cacgaccgtg     780
```

| | |
|---|---|
| accgtgagcg cggctagcac caagggccca tcggtcttcc ccctggcacc ctcctccaag | 840 |
| agcacctctg ggggcacagc ggccctgggc tgcctggtca aggactactt ccccgaaccg | 900 |
| gtgacggtgt cgtggaactc aggcgccctg accagcggcg tgcacacctt cccggctgtc | 960 |
| ctacagtcct caggactcta ctccctcagc agcgtggtga ccgtgccctc agcagcttg | 1020 |
| ggcacccaga cctacatctg caacgtgaat cacaagccca gcaacaccaa ggtggacaag | 1080 |
| agagttgagc ccaaatcttg tgacaaaact cacacatgcc caccgtgccc agcacctgaa | 1140 |
| ctcctggggg gaccgtcagt cttcctcttc cccccaaaac ccaaggacac cctcatgatc | 1200 |
| tcccggaccc ctgaggtcac atgcgtggtg gtggacgtga gccacgaaga ccctgaggtc | 1260 |
| aagttcaact ggtatgtgga cggcgtggag gtgcataatg ccaagacaaa gccgcgggag | 1320 |
| gagcagtaca acgccacgta ccgtgtggtc agcgtcctca ccgtcctgca ccaagactgg | 1380 |
| ctgaatggca aggagtacaa gtgcaaggtc tccaacaaag ccctcccagc ccccatcgcc | 1440 |
| gcaaccatct ccaaagccaa agggcagccc cgagaaccac aggtgtacac cctgccccca | 1500 |
| tcccgggagg agatgaccaa gaaccaagtc agcctgacct gcctggtcaa aggcttctat | 1560 |
| cccagcgaca tcgccgtgga gtgggagagc aatgggcagc cggagaacaa ctacaagacc | 1620 |
| acgcctcccg tgctggactc cgacggctcc ttcttcctct attccaagct caccgtggac | 1680 |
| aagagcaggt ggcagcaggg gaacgtcttc tcatgctccg tgatgcatga ggctctgcac | 1740 |
| aaccactaca cgcagaagag cctctccctg tctccgggca atga | 1785 |

<210> SEQ ID NO 12
<211> LENGTH: 642
<212> TYPE: DNA
<213> ORGANISM: Artificial Sequence
<220> FEATURE:
<223> OTHER INFORMATION: light chain

<400> SEQUENCE: 12

| | |
|---|---|
| cagatcgtgc tgagccagtc gccggccatc ctcagcgcga gccccggcga aaggtcacc | 60 |
| atgacgtgcc gggccagcag ctcggtgagc tacatccact ggttccagca aagcccggg | 120 |
| agcagcccca gccgtggat ctacgccacc agcaacctgg cctcgggcgt gcccgtgcgc | 180 |
| ttcagcggga gcggcagcgg gaccagctac agcctgacca tctcgcgggt cgaggccgag | 240 |
| gacgccgcca cctactactg ccagcagtgg acctccaacc cgcccacgtt cggcggcggc | 300 |
| accaagcacg agctgaagcg aactgtggct gcaccatctg tcttcatctt cccgccatct | 360 |
| gatgagcagt tgaaatctgg aactgcctct gttgtgtgcc tgctgaataa cttctatccc | 420 |
| agagaggcca aagtacagtg gaaggtggat aacgccctcc aatcgggtaa ctcccaggag | 480 |
| agtgtcacag agcaggacag caaggacagc acctacagcc tcagcagcac cctgacgctg | 540 |
| agcaaagcag actacgagaa acacaaagtc tacgcctgcg aagtcaccca tcagggcctg | 600 |
| agctcgcccg tcacaaagag cttcaacagg ggagagtgtt ag | 642 |

<210> SEQ ID NO 13
<211> LENGTH: 594
<212> TYPE: PRT
<213> ORGANISM: Artificial Sequence
<220> FEATURE:
<223> OTHER INFORMATION: SD1-heavy chain

<400> SEQUENCE: 13

Glu Glu Glu Leu Gln Val Ile Gln Pro Asp Lys Ser Val Ser Val Ala
1               5                   10                  15

```
Ala Gly Glu Ser Ala Ile Leu His Cys Thr Val Thr Ser Leu Ile Pro
             20                  25                  30

Val Gly Pro Ile Gln Trp Phe Arg Gly Ala Gly Pro Ala Arg Glu Leu
         35                  40                  45

Ile Tyr Asn Gln Lys Glu Gly His Phe Pro Arg Val Thr Thr Val Ser
     50                  55                  60

Glu Ser Thr Lys Arg Glu Asn Met Asp Phe Ser Ile Ser Ile Ser Ala
 65              70                  75                      80

Ile Thr Pro Ala Asp Ala Gly Thr Tyr Tyr Cys Val Lys Phe Arg Lys
                 85                  90                  95

Gly Ser Pro Asp Thr Glu Phe Lys Ser Gly Ala Gly Thr Glu Leu Ser
                100                 105                 110

Val Arg Ala Lys Pro Ser Ala Pro Val Val Ser Gly Pro Ala Ala Arg
            115                 120                 125

Ala Thr Pro Gln His Gly Gly Gly Ser Gly Gly Gly Gly Ser Gln
            130                 135                 140

Val Gln Leu Gln Gln Pro Gly Ala Glu Leu Val Lys Pro Gly Ala Ser
145                 150                 155                 160

Val Lys Met Ser Cys Lys Ala Ser Gly Tyr Thr Phe Thr Ser Tyr Asn
                165                 170                 175

Met His Trp Val Lys Gln Thr Pro Gly Arg Gly Leu Glu Trp Ile Gly
                180                 185                 190

Ala Ile Tyr Pro Gly Asn Gly Asp Thr Ser Tyr Asn Gln Lys Phe Lys
            195                 200                 205

Gly Lys Ala Thr Leu Thr Ala Asp Lys Ser Ser Ser Thr Ala Tyr Met
    210                 215                 220

Gln Leu Ser Ser Leu Thr Ser Glu Asp Ser Ala Val Tyr Tyr Cys Ala
225                 230                 235                 240

Arg Ser Thr Tyr Tyr Gly Gly Asp Trp Tyr Phe Asn Val Trp Gly Ala
                245                 250                 255

Gly Thr Thr Val Thr Val Ser Ala Ala Ser Thr Lys Gly Pro Ser Val
            260                 265                 270

Phe Pro Leu Ala Pro Ser Ser Lys Ser Thr Ser Gly Gly Thr Ala Ala
        275                 280                 285

Leu Gly Cys Leu Val Lys Asp Tyr Phe Pro Glu Pro Val Thr Val Ser
    290                 295                 300

Trp Asn Ser Gly Ala Leu Thr Ser Gly Val His Thr Phe Pro Ala Val
305                 310                 315                 320

Leu Gln Ser Ser Gly Leu Tyr Ser Leu Ser Ser Val Val Thr Val Pro
                325                 330                 335

Ser Ser Ser Leu Gly Thr Gln Thr Tyr Ile Cys Asn Val Asn His Lys
            340                 345                 350

Pro Ser Asn Thr Lys Val Asp Lys Arg Val Glu Pro Lys Ser Cys Asp
        355                 360                 365

Lys Thr His Thr Cys Pro Pro Cys Pro Ala Pro Glu Leu Leu Gly Gly
        370                 375                 380

Pro Ser Val Phe Leu Phe Pro Pro Lys Pro Lys Asp Thr Leu Met Ile
385                 390                 395                 400

Ser Arg Thr Pro Glu Val Thr Cys Val Val Val Asp Val Ser His Glu
                405                 410                 415

Asp Pro Glu Val Lys Phe Asn Trp Tyr Val Asp Gly Val Glu Val His
            420                 425                 430

Asn Ala Lys Thr Lys Pro Arg Glu Glu Gln Tyr Asn Ala Thr Tyr Arg
```

```
                    435                 440                 445
Val Val Ser Val Leu Thr Val Leu His Gln Asp Trp Leu Asn Gly Lys
    450                 455                 460

Glu Tyr Lys Cys Lys Val Ser Asn Lys Ala Leu Pro Ala Pro Ile Ala
465                 470                 475                 480

Ala Thr Ile Ser Lys Ala Lys Gly Gln Pro Arg Glu Pro Gln Val Tyr
                485                 490                 495

Thr Leu Pro Pro Ser Arg Glu Glu Met Thr Lys Asn Gln Val Ser Leu
            500                 505                 510

Thr Cys Leu Val Lys Gly Phe Tyr Pro Ser Asp Ile Ala Val Glu Trp
        515                 520                 525

Glu Ser Asn Gly Gln Pro Glu Asn Asn Tyr Lys Thr Thr Pro Pro Val
    530                 535                 540

Leu Asp Ser Asp Gly Ser Phe Phe Leu Tyr Ser Lys Leu Thr Val Asp
545                 550                 555                 560

Lys Ser Arg Trp Gln Gln Gly Asn Val Phe Ser Cys Ser Val Met His
                565                 570                 575

Glu Ala Leu His Asn His Tyr Thr Gln Lys Ser Leu Ser Leu Ser Pro
            580                 585                 590

Gly Lys
```